(12) United States Patent
Sherley et al.

(10) Patent No.: US 8,404,481 B2
(45) Date of Patent: *Mar. 26, 2013

(54) HEPATOCYTE PRECURSOR CELL LINES

(75) Inventors: James L. Sherley, Boston, MA (US); Hsuan-Shu Lee, Taipei (TW); Gracy G. Crane, Allston, MA (US)

(73) Assignee: Massachusetts Institute of Technology, Cambridge, WA (US)

( * ) Notice: Subject to any disclaimer, the term of this patent is extended or adjusted under 35 U.S.C. 154(b) by 484 days.

This patent is subject to a terminal disclaimer.

(21) Appl. No.: 12/619,107

(22) Filed: Nov. 16, 2009

(65) Prior Publication Data

US 2010/0086936 A1 Apr. 8, 2010

Related U.S. Application Data

(63) Continuation of application No. 10/369,428, filed on Feb. 18, 2003, now Pat. No. 7,645,610.

(60) Provisional application No. 60/357,543, filed on Feb. 15, 2002.

(51) Int. Cl.
*C12N 5/00* (2006.01)
*C12N 5/02* (2006.01)
*C12N 5/07* (2010.01)
*C12N 5/071* (2010.01)

(52) U.S. Cl. .................. 435/370; 435/375; 435/377

(58) Field of Classification Search .................. None
See application file for complete search history.

(56) References Cited

U.S. PATENT DOCUMENTS

| 5,474,931 | A | | 12/1995 | DiSorbo et al. | |
|---|---|---|---|---|---|
| 5,741,646 | A | * | 4/1998 | Sherley et al. | 435/6.16 |
| 5,801,159 | A | * | 9/1998 | Miller et al. | 514/45 |
| 6,146,889 | A | * | 11/2000 | Reid et al. | 435/325 |
| 6,242,252 | B1 | * | 6/2001 | Reid et al. | 435/325 |
| 6,458,589 | B1 | * | 10/2002 | Rambhatla et al. | 435/370 |
| 7,645,610 | B2 | * | 1/2010 | Sherley et al. | 435/370 |
| 7,824,912 | B2 | * | 11/2010 | Sherley et al. | 435/326 |
| 2003/0133918 | A1 | | 7/2003 | Sherley | |
| 2005/0074874 | A1 | | 4/2005 | Sherley | |

FOREIGN PATENT DOCUMENTS

| WO | 97/24458 A1 | 7/1997 |
|---|---|---|
| WO | 02/062969 A2 | 8/2002 |
| WO | 03/006613 A2 | 1/2003 |
| WO | 03/069972 A2 | 8/2003 |

OTHER PUBLICATIONS

ATCC Catalogue, 8th Edition:518 (1994). "ATCC Cell Lines and Hybridomas."
Bartel et al., Biochimica et Biophysica Acta., 1035:331-339 (1990).
Brenner, M.K., New England Journal of Medicine, 335(5):337-339 (1996). "Gene Transfer to Hematopoietic Cells."
Cairns, J., Nature, 255:197-200 (1975). "Mutation selection and the natural history of cancer."
Fuchs, E. and Segre, J.A., Cell, 100:143-155 (2000). "Stem Cells: A New Lease on Life."
Ganassin et al., Journal of Cellular Physiology, 160:409-416 (1994). "Enhancement of Proliferation in Cultures of Chinook Salmon Embryo Cells by Interactions Between Inosine and Bovine Sera."
Gridelli, B. and Giuseppe, R., The New England Journal of Medicine, pp. 404-410 (2000). "Strategies for Making More Organs Available for Transplantation."
Hayashi et al., Experimental Cell Research, 185:217-228 (1989). "Fibroblast Growth Factor-Stimulated Growth of Porcine Aortic Endothelial Cells Depends on Hypoxanthine in Fetal Bovine Serum in Culture Media."
Hirai et al., Biochemical Pharmacology, 45(8:1695-1701 (1993). "Fibroblast Growth Factor-Dependent Metabolism of Hypoxanthine Via the Salvage Pathway for Purine Synthesis in Porcine Aortic Endothelial Cells."
Lee et al., Biotech. and Bioeng., 83(7): 760-771 (2003). "Clonal Expansion of Adult Rat Hepatic Stem Cell Lines by Suppression of Asymmetric Cell Kinetics (SACK)."
Liu et al., Journal of Cellular Physiology, 177: 364-376 (1998). "Comparison of bax, waf1, and IMP Dehydrogenase Regulation in Response to Wild-Type p53 Expression Under Normal Growth Conditions."
Liu et al., Molecular Biology of the Cell, 9(1):15-28.
Loeffler, M. and Potten, C., Stem Cells, pp. 1-28 (1997). "Stem cells and cellular pedigrees—a conceptual introduction."
Merok, J. and Sherley, J.L., Journal of Biomedicine and Biotechnology, 1:25-27 (2001). "Breaching the kinetic barrier to in vitro somatic stem cell propogation."
Moore et al., Blood, 89(12):4337-4347 (1997). "In Vitro Maintenance of Highly Purified, Transplantable Hematopoietic Stem Cells."
Phillips et al., Science, 288:1635-1640 (2000). "Genetic Program of Hematopoietic Stem Cells."
Podolsky, D.K., American Journal of Physiology, 264:G179-G186 (1993). "Regulation of intestinal epithelial proliferation: a few answers, many questions."
Potten, C.S. and Grant, H.K., British Journal of Cancer, 78(8): 993-1003 (1998). "The relationship between ionizing radiation-induced apoptosis and stem cells in the small and large intestine."
Potten, C.S. and Morris, R.J., J. Cell Sci. Suppl., 10:45-62 (1988). "Epithelial stem cells In vivo."
Rambhatla et al., Journal of Biomedicine and Biotechnology, 1(1):28-37 (2001).
Reisner et al., Proc. Natl. Acad. Sci. USA, 75:2933-2936 (1978). "Hemopoietic stem cell transplantation using mouse bone marrow and spleen cells fractionated by lectins."
Sherley et al., Cell Prolif., 28:137-144 (1995). "A quantitative method for the analysis of mammalian cell proliferation in culture in terms of dividing and non-dividing cells."
Sherley et al., Proc. Natl. Acad. Sci. USA, 92:136-140 (1995). "Expression of the wild-type p53 antioncogene induces guanine nucleotide-dependent stem cell division kinetics."

(Continued)

*Primary Examiner* — Vera Afremova
(74) *Attorney, Agent, or Firm* — Nixon Peabody LLP; Ronald I. Eisenstein; David S. Resnick

(57) ABSTRACT

The present invention is directed to methods for readily generating hepatocyte precursor cell lines that retain hepatocyte-specific functions after extensive in vitro culturing. The methods comprise isolating and culturing hepatocyte precursor cell lines under permissive culture conditions that suppress asymmetric cell kinetics and allow exponential growth of the precursor cells, followed by transferring the hepatocyte precursor cell lines to non-permissive culture conditions that allow expression of asymmetric cell kinetics and induce expression of hepatocyte-specific characteristics.

6 Claims, 13 Drawing Sheets

OTHER PUBLICATIONS

Sherley, J.L. "Adult Stem Cell Differentiation" What Does It Mean? Published Online.
Sherley, J.L. Abstract, pg. CARB 10 (2000). "IMPDH: A Regulator of Somatic Stem Cell Kinetics."Sherley, J.L. Abstract, pg. CARB 10 (2000). "IMPDH: A Regulator of Somatic Stem Cell Kinetics."
Sherley, J.L. The Journal of Biological Chemistry, pp. 24815-24828 (1991). "Guanine Nucleotide Biosynthesis Is Regulated by the Cellular p53 Concentration."
Stryer, L., Biochemistry, Second edition, p. 514 (1981).
Talbot et al., Cloning and Stem, 6(1):37-47 (2004). "Comparision of Colony-Formation Efficiency of Bovine Fetal Fibroblast Cell Lines Cultured with Low Oxygen, Hydrocortisone, L-Carnosine, bFGF, or Different Levels of FBS."
Tunstead et al., Abstract, Dev. Bio., 235(1):227 (2001). "Molecular Determinants of Asymmetric Stem Cell Kinetics."
Wagers et al., Cell, 116:639-648 (2004). "Plasticity of Adult Stem Cells."
Weissman, I.L., Cell, 100:157-168 (2000). "Stem Cells: Units of Development, Units of Regeneration, and Units of Evolution."
Wilson, J.M., Nature, 365:691-692 (1993). "Vehicles for gene therapy."
Zimmerman et al., Leukemia, 17:1146-1149 (2003). "Lack of telomerase activity in human mesenchymal stem cells."

* cited by examiner

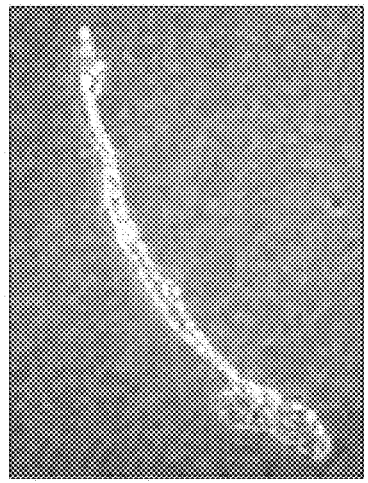
FIG. 8A
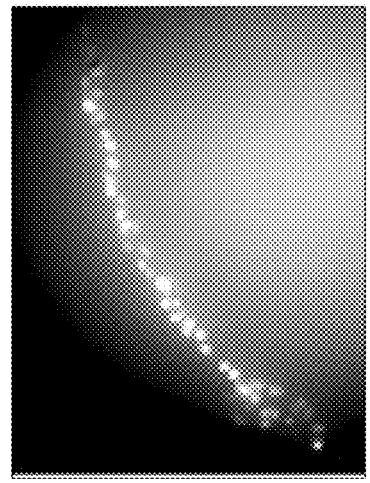
FIG. 8B
FIG. 8C
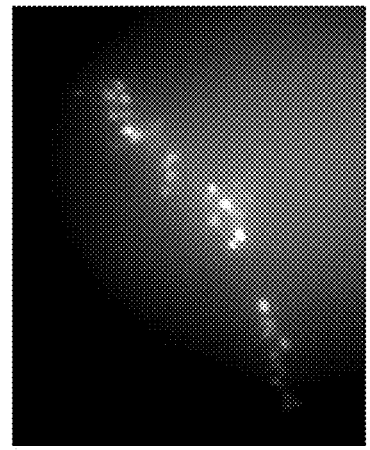
FIG. 8D

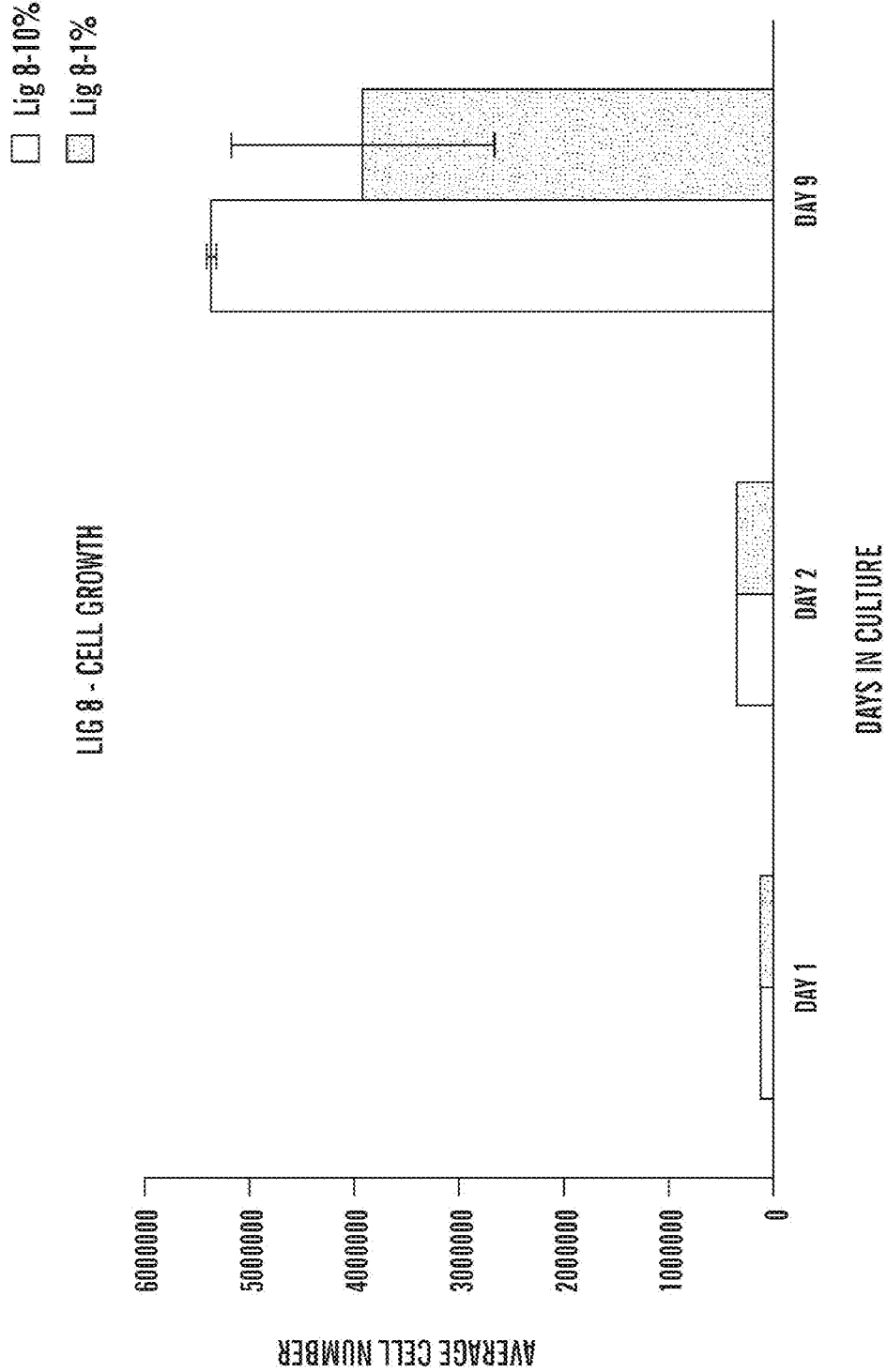

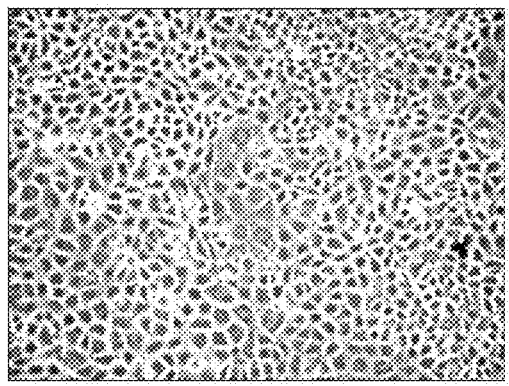 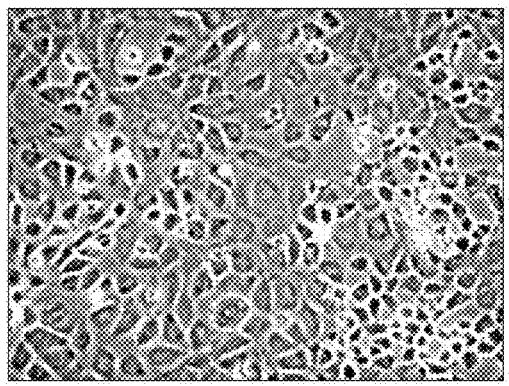
Lig 8-10% SERUM (10X MAG)
FIG. 10A
Lig 8-1% SERUM (10X MAG)
FIG. 10B
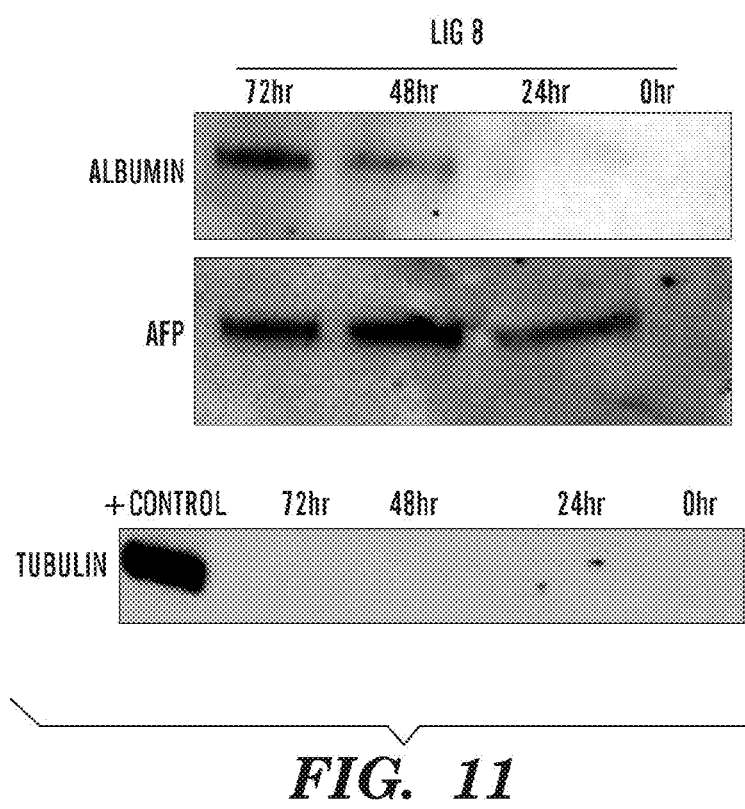
FIG. 11

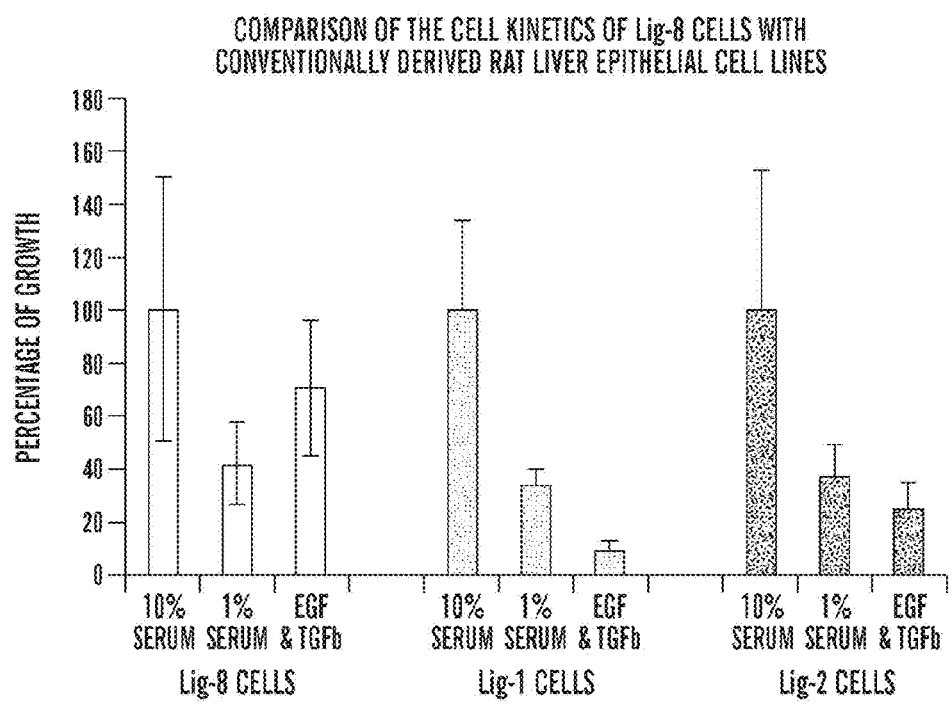
*FIG. 13*
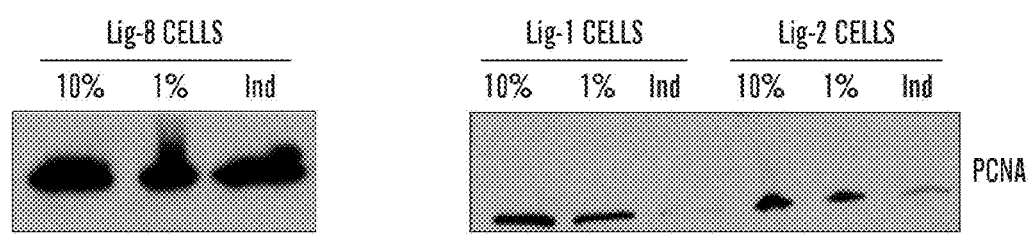
*FIG. 14A*   *FIG. 14B*

HEPATOCYTE PRECURSOR CELL LINES

CROSS REFERENCE TO RELATED APPLICATIONS

This application is a continuation application of U.S. Ser. No. 10/369,428 filed Feb. 18, 2003, which claims the benefit of priority under 35 U.S.C. §119(e) of U.S. Provisional Application No. 60/357,543, filed Feb. 15, 2002, the contents of which are incorporated herein by reference in its entirety.

FIELD OF THE INVENTION

The present application is directed to the isolation of hepatocyte precursor cell lines from a mammalian tissue, preferably somatic stem cells from human tissue.

BACKGROUND OF THE INVENTION

Considerable attention has focused on stem cells and their uses in a range of therapies. For example, the gap between the need for replacement of damaged or diseased organs in patients, with otherwise significant life-expectancy, and the supply of donor organs is growing at an ever increasing rate (Gridelli and Remuzzi, 2000). Tissue bioengineering and in vitro organogenesis research have the potential to bridge this gap. The availability of stem cells for organs in demand would greatly accelerate progress in these efforts. Age-dependent changes in stem cell function are predicted to contribute to the aging of human tissues (Merok and Sherley, 2001; Rambhatla et al., 2001). Stem cells are also ideal delivery vessels for gene therapy (Wilson, 1993; Brenner, 1996). In theory, after genetic engineering such stem cells would persist in a tissue while producing differentiated tissue constituent cells that would supply therapeutic gene expression.

The availability of liver stem cells that could give rise to mature functioning hepatocytes and other hepatic cells is particularly desirable. Hepatocyte transplantation has been proposed as a potential therapeutic method to treat irreversible liver failure and inherited hepatic disorders (Fujino et al., *Cell Transplantation* 10: 353-66 (2001)). In children, the most common indications of severe, irreversible liver disease are biliary atresia, a condition which leads to distortion of bile ducts and liver cirrhosis, and genetically transmitted metabolic disorders which may lead to hepatic failure and/or cirrhosis. Adults suffering from nonalcoholic or alcoholic cirrhosis as well as liver cancer are also transplantation candidates. Medical and surgical treatments often fail these patients.

One of the major limitations of hepatocyte transplantation therapy is the serious shortage of donor livers for hepatocyte isolation (Kobayashi et al., *Cell Transplantation* 10: 377-81 (2001)). An ideal alternative to primary human hepatocytes would be to use a clonal hepatocyte precursor cell line that grows in culture and retains the ability to express characteristics of differentiated, nontransformed hepatocytes following transplantation.

Such a precursor cell line has also been proposed as an attractive alternative to the use of primary human hepatocytes for developing a bioartificial, or hybrid artificial, liver (Kobayashi et al., *Cell Transplantation* 10: 377-81 (2001); Kobayashi et al., *Cell Transplantation* 10: 387-92 (2001)).

The liver is also a well-studied target organ for human gene therapy. For example, much attention has focused on the use of the liver as a target for gene therapy to treat diabetes. (Mulligan, *Science* 260:926-32 (1993); Crystal, *Science* 270: 404-410 (1995)).

Beyond their potential therapeutic applications, portable, stable cell lines that retain hepatocyte-specific metabolic activities would also be highly desirable to support development of human-specific drug metabolism assays.

Accordingly, methods to isolate and expand precursor stem cells, particularly without significant differentiation, are highly desirable. The availability of hepatocyte precursor stem cell lines would greatly contribute to cell replacement therapies such as liver cell transplants, gene therapies, tissue engineering, and in vitro organogenesis. Production of autologous stem cells to replace injured tissue would also reduce the need for immune suppression interventions. However, considerable difficulty in achieving this objective has been encountered thus far.

Cell growth is a carefully regulated process that responds to the specific needs of the body in different tissues and at different stages of development. In a young animal, cell multiplication exceeds cell loss and the animal increases in size; in an adult, the processes of cell division and cell loss are balanced to maintain a steady state. For some adult cell types, renewal is rapid: intestinal cells and certain white blood cells have a half-life of a few days before they die and are replaced. In contrast, the half-life of human red blood cells is approximately 100 days; healthy liver cells rarely die, and in adults, there is a slow loss of brain cells with little or no replacement.

Somatic stem cells possess the ability to renew adult tissues (Fuchs and Segre, 2000). The predominant way somatic stem cells divide is by asymmetric cell kinetics (see FIG. 1). During asymmetric kinetics, one daughter cell divides with the same kinetics as its stem cell parent, while the second daughter gives rise to a differentiating non-dividing cell lineage. The second daughter may differentiate immediately; or, depending on the tissue, it may undergo a finite number of successive symmetric divisions to give rise to a larger pool of differentiating cells.

Attempts at deriving hepatocyte precursor stem cell isolation have been described, for example, in studies to enrich for hematopoietic stem cells (Phillips et al., 2000). However, although high degrees of enrichment have been reported, so far somatic stem cells, including hepatocyte precursor stem cells, have neither been identified nor purified to homogeneity. A major obstacle to these two challenges is the inability to expand HSCs in culture.

Attempts at propagating somatic stem cells have encountered a number of significant difficulties. The asymmetric cell kinetics which are a defining characteristic of somatic stem cells are also a major obstacle to their expansion in vitro (FIG. 1) (Merok and Sherley, 2001; Rambhatla et al., 2001). In culture, continued asymmetric cell kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution.

Even in instances where it is possible to select for relatively purer populations such as hematopoietic stem cells (for example by cell sorting), these populations do not expand when cultured.

The liver contains several resident cell types in addition to hepatocytes, including stellate cells, cholangiocytes, oval cells, Kupffer cells, and sinusoidal endothelial cells (Alpini et al., 1994). In the adult liver, the majority of liver cells are hepatocytes, with stellate cells and cholangiocytes representing minority populations of cells (Grompe et al., 2001). Stellate cells function as the primary source of extracellular matrix in normal and diseased liver, transitioning from a quiescent vitamin-A rich cell to a highly fibrogenic cell during activation caused by liver injury. Cholangiocytes line the intrahepatic biliary tree inside the liver. Cholangiocytes play a key role in the modification of bile, secreted by hepatocytes, by a series of reabsorbtive and secretory processes under both spontaneous and hormone-regulated conditions. Cholangiocytes also have the ability to selectively proliferate during injury such as bile duct ligation. Oval cells are found in the periportal region of the liver under some conditions, and have been postulated to function as a bi-potential precursor cell with the ability to give rise to hepatocytes and cholangiocytes (also known as bile duct cells).

The possible existence of renewing stem cells in adult liver has been hotly contested for many years. Because mature hepatocytes divide in response to liver injury, many have considered their division to provide the renewing stem cell function for adult liver. Although a well-defined hepatocyte stem cell turnover unit has been elusive, it is clear that both cell division and apoptosis do occur in adult liver.

Recent studies in rodents indicate that hepatocyte stem cells (derived from the mesoderm) may be able to home to the liver after it is damaged, and demonstrate plasticity in becoming hepatocytes (usually derived from the endoderm). Lagasse et al., *Nat. Med.* 6:1229-34 (2000); Petersen et al., *Science* 284: 1168-70 (1999); Theise et al., *Hepatology* 32: 11-16 (2000). However, there is no clear indication that cells from the bone marrow normally generate hepatocytes in vivo. Moreover, it is not known whether this kind of plasticity occurs without severe damage to the liver or whether hepatocyte stem cells from the bone marrow generate oval cells of the liver. Crosby et al., *Gut* 48:153-4 (2001). Although hepatic oval cells exist in injured livers, it is not clear whether they actually generate new hepatocytes. Indeed, hepatocytes themselves may be responsible for the well-known regenerative capacity of the liver.

The possible existence of a "transitional stem cell" in liver that is capable of giving rise to both hepatocyte and bile epithelial precursor cells has also been suggested. Although bi-potent progenitor cells of this type have been described during embryonic liver development (Zaret, *Ann. Rev. Physiol.* 58: 231-251 (1996); Sell, *Modern. Pathol.* 7: 105-112 (1994)), there is no clear indication that this cell exists in the adult liver. Oval cells are found in the periportal region of the liver under some conditions and may represent such a bi-potent progenitor cell.

Previously, rat liver-derived cell lines have been described from three different liver states, fetal liver, pathological liver (i.e., oval cells), and normal adult liver. The best described of these is the clonally-derived line WB-F344, which was isolated from an adult rat (Tsao et al., *Exp. Cell Res.* 154: 38-52 (1984)). WB-F344 cells have many properties indicative of hepatocyte stem cell origin and have been cited as the best evidence for the existence liver stem cells. These cells express several markers of hepatocyte and biliary origin. When transplanted in vivo, WB-F344 cells have been shown to integrate into hepatic plates and express hepatocyte specific marker proteins. However, WB-F344 cells phenotypically most closely resemble oval cells and do not represent a true hepatocyte precursor cell line. For example, they express oval cell-specific antigens, like OV6, which are not expressed by mature hepatocytes (Grisham et al., *P.S.E.B.M.* 204: 270-279 (1993); Grompe et al., "Liver Stem Cells" in *Stem Cell Biology*, Marshak, Gardner, and Gottleib, eds. CSHL Press (Cold Spring Harbor) pp. 455-497 (2001)).

Accordingly, it would be particularly desirable to have a source of hepatocyte precursor stem cells, including hepatocyte progenitor cells which can be expanded in vitro and express hepatocyte-specific characteristics, including metabolic activities, as well as cholangiocyte progenitor cells which can be expanded in vitro and express cholangiocyte-specific characteristics.

SUMMARY OF THE INVENTION

We have now discovered methods for readily generating hepatocyte precursor cell lines that retain cell type-specific functions after extensive in vitro culturing. Such a precursor cell can not only differentiate into a hepatocyte stem cell, it can also differentiate into other hepatic cells such as cholangiocyte stem cells. The hepatocyte precursor cell sometimes also referred to as a hepatic precursor cell. Typically, the differentiation can mirror the relative proportion of the various hepatic cells in vivo. The methods comprise isolating and culturing hepatocyte precursor cell lines under permissive culture conditions that suppress asymmetric cell kinetics and allow exponential growth of the precursor cells, followed by transferring the precursor cell lines to non-permissive culture conditions that allow expression of asymmetric cell kinetics and induce expression of hepatocyte-specific characteristics.

The method of the present invention provides for deriving clonal lines of hepatocyte precursor cell lines by limiting dilution plating or single cell sorting under conditions which enhance guanine nucleotide biosynthesis, thereby suppressing asymmetric cell kinetics. In one preferred embodiment, the hepatic precursor cell lines are hepatocyte progenitor cells which can be expanded in vitro and express hepatocyte-specific characteristics, including metabolic activities. In another preferred embodiment, the hepatic stem cells are cholangiocyte precursor stem cells which can be expanded in vitro and express cholangiocyte-specific characteristics.

The methods comprise isolating and culturing hepatocyte precursor cells under permissive culture conditions that suppress asymmetric cell kinetics and allow exponential growth of the precursor cells by enhancing guanine nucleotide (GNP) biosynthesis, thereby expanding guanine nucleotide pools. This in turn conditionally suppresses asymmetric cell kinetics in the hepatocyte precursor cells. The methods of the invention include pharmacological methods and genetic methods. One preferred method of enhancing guanine nucleotide biosynthesis is to bypass or override normal inosine-5'-monophosphate dehydrogenase (IMPDH) regulation. IMPDH catalyzes the conversion of inosine-5' monophosphate (IMP) to xanthosine monophosphate (XMP) for guanine nucleotide biosynthesis. This step can be bypassed or overridden by providing a guanine nucleotide precursor (rGNPr) such as xanthosine or hypoxanthine, respectively. The next metabolite in the GNP pathway is guanine monophosphate (GMP), which in turn is metabolized to the cellular guanine nucleotides. The resulting cultured hepatocyte precursor cells can be used for a variety of applications including cell replacement therapies such as gene therapies, tissue engineering, and in vitro organogenesis.

In one preferred embodiment of the invention, hepatocyte precursor cells are removed and cultivated in the presence of compounds such as guanine nucleotide precursors (rGNPrs), which lead to increased guanine nucleotide pools. Preferably, the rGNPr is xanthosine or hypoxanthine. Even more preferably, the rGNPr is xanthosine.

In another embodiment of the invention, genes that lead to constitutive upregulation of guanine ribonucleotides (rGNPs) are introduced into the hepatocyte precursor cells. Preferred genes are those that encode inosine-5' monophosphate dehydrogenase (IMPDH) or xanthine phosphoribosyltransferase (XPRT). More preferably, XPRT.

In another preferred embodiment of the invention, the hepatocyte precursor cells are propagated in a primitive undifferentiated state but retain the ability to be induced to produce differentiating progeny cells.

In one preferred embodiment of the invention, the hepatocyte precursor cell lines express the following characteristics of differentiated hepatocytes upon culturing in non-permissive conditions: growth arrest after serum reduction, reduced expression α-fetoprotein, induced expression of hepatocyte-specific protein albumin and H4 antigen, expression of cytochrome p450 1A1 activity, and microvilli formation.

In another preferred embodiment of the invention, the hepatocyte precursor stem cell lines retain the ability to differentiate into mature hepatocytes after at least 80 cell doublings under permissive conditions that suppress asymmetric cell kinetics.

BRIEF DESCRIPTION OF THE DRAWINGS

FIGS. 2A-C, DAPI fluorescence to detect daughter cell nuclei; FIGS. 2a-c, in situ immunofluorescence analysis to detect BrdU(+) daughters.

FIG. 4 shows immunoblot analysis of Albumin expression in conventional and Xs-derived adult hepatic epithelial cell lines.

FIG. 5A: Immunoblot analyses for albumin and AFP in Lig-8 culture supernatants. Supernatants were also analyzed for β-tubulin as a control for cell lysis. "+control", 25 µgrams of cell lysate protein as a marker for tubulin protein. FIG. 5B: Immunoblot analyses for albumin and AFP in culture supernatants of Lig-1, Lig-2, and Lig-13 cells.

FIG. 6A: Immunoblot analyses of CK7, a cholangiocyte marker, in cell lysates (20 µg protein) from conventional (Lig-1 and Lig-2) and Xs-derived (Lig-8 and Lig-13) cell lines. The membrane was re-probed with anti-β-tubulin antibodies to verify extract loading. FIG. 6B: Immunoblot analysis of alpha-1 antitrypsin (AAT), a mature hepatocyte marker. Xs-derived cells were cultured in Xs-free (Xs−) or Xs-supplemented medium (Xs+). The membrane was re-probed with anti-CK7 antibodies.

FIG. 7C shows a phase contrast micrograph of binucleated cells recovered from culture supernatants of quiescent cultures of Lig-8 cells.

FIGS. 8A-8D are micrographs showing production of tubular structures by Lig-13 cells, a putative adult rat cholangiocyte stem cell line. FIGS. 8A and 8B: Phase contrast micrographs of two examples of structures formed by Lig-13 cells cultured for 2 weeks in soft agar. FIGS. 8C and 8D: Epifluorescence visualization of cell nuclei in structures in A and B stained with the fluorescent DNA dye DAPI. In B, there appears to be lumen formation surrounded by cell bodies.

FIG. 9 is graph showing the growth of Lig-8 cells. Lig-8 cells were grown in culture medium supplemented with 10% and 1% dialyzed fetal bovine serum. The cells continued to proliferate in culture medium supplemented with 1% dialyzed fetal bovine serum.

FIGS. 10A and 10B are micrographs showing the morphology of Lig-8 cells grown in culture medium supplemented with 10% and 1% dialyzed fetal bovine serum. In FIG. 10A, the culture was supplemented with 10% dialyzed fetal bovine serum, and Lig-8 cells exhibited a epithelial morphology. In FIG. 10B, the culture was supplemented with 1% dialyzed fetal bovine serum, and the cells were larger, with more binucleated cells observed.

FIG. 11 shows the secretion of Albumin and AFP by Lig-8 cells. Lig-8 cells were grown in medium sipplemented with 10% dialyzed fetal bovine serum. When the cells were confluent, the medium containing 10% dialyzed fetal bovine serum was removed and medium without serum was added. Aliquots of the medium were decanted at 24 hour intervals and expression of secretory proteins albumin and AFP was measured by immunoblotting. Tubulin was used as a control marker to detect proteins that were released into the medium due to cell lysis rather than secreted into the medium.

In FIG. 12A, Lig-8 cells were induced to differentiate by the addition of EGF and TGF-β to cells growing in medium supplemented with 1% dialyzed serum. The high density cultures had a heterogeneous cell population, as shown in FIG. 12B. In the low density culture shown in FIG. 12C, most of the cells showed the morphological changes associated with differentiation (the presence of bi-nucleated cells).

FIG. 13 is a graph comparing the cell kinetics of Lig-8 cells treated with EGF and TGF-β with conventionally derived rat liver epithelial cell lines (Lig-1 and Lig-2). Addition of the growth factors to the conventionally derived cell lines resulted in a dramatic suppression of the overall growth rate (80-90% reduced). In contrast, addition of the growth factors to Lig-8 cells resulted in only a modest (30%) reduction in overall cell growth rate.

FIGS. 14A and 14B are immunoblots showing expression of PCNA, which was used as an additional indicator of the cell kinetics state of treated Lig-8 cells. High levels of PCNA expression is indicative of active cycling cells. FIG. 14A shows expression of PCNA in Lig-8 cells. FIG. 14B shows expression of PCNA in two control cell lines, Lig-1 and Lig-2 cells.

In FIG. 15A, AFP, alpha 1-antitrypsin and albumin were analyzed in EGF and TGF-β treated cells by immunoblotting. FIG. 15B shows the expression of 3 transcription factors, HNF3, C/EBP α and C/EBP β, analyzed by immunoblotting.

DETAILED DESCRIPTION OF THE INVENTION

Figure 1:
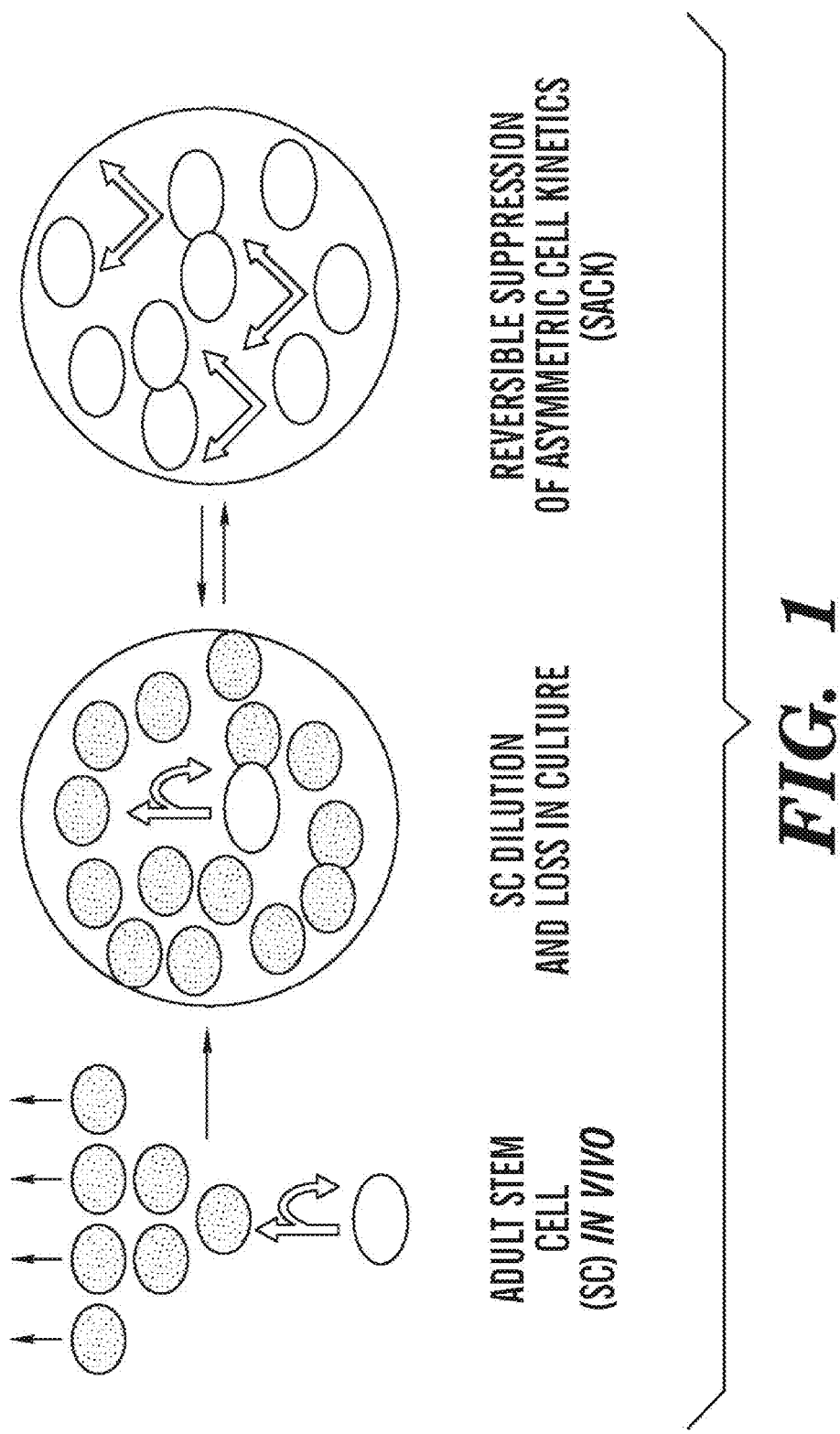
FIG. 1 illustrates the SACK strategy. Adult stem cells in vivo divide with asymmetric cell kinetics to yield progeny that differentiate and eventually produce terminally arrested cells. In vivo, this kinetics program provides for tissue cell differentiation and renewal while preserving a constant stem cell number. When tissue units are explanted and cultured ex vivo, the same kinetics program leads to the dilution and loss of stem cells due to the accumulation of progeny that undergo terminal division arrest. By converting adult stem cells to symmetric cell kinetics in culture, SACK agents promote their exponential expansion and stable propagation in culture. Because cell kinetics effects of SACK agents are reversible (double arrows), after their removal, it is possible to subsequently evaluate the differentiation properties of adult stem cell progeny.

We have now discovered methods for propagating somatic stem cells ex vivo by enhancing guanine nucleotide biosynthesis, thereby expanding guanine nucleotide pools, and conditionally suppressing asymmetric cell kinetics in the explanted stem cells. The methods of the invention include pharmacological methods and genetic methods. Somatic stem cells can be used for a variety of applications, including cell replacement therapies such as bone marrow transplants, gene therapies, tissue engineering, and in vitro organogenesis.

The present invention provides methods for readily generating hepatocyte precursor cell lines that retain cell type-specific functions after extensive in vitro culturing. Such precursor cell lines can produce progeny cells that differentiate to express hepatocyte cell properties; they can also produce progeny cells that differentiate into other hepatic cell types such as cholangiocyte stem cells. The methods comprise isolating and culturing hepatocyte precursor cell lines under permissive culture conditions that suppress asymmetric cell kinetics and allow exponential growth of the precursor cells, followed by transferring the precursor cell lines to nonpermissive culture conditions that allow expression of asymmetric cell kinetics and induce expression of specific hepatic cell type characteristics. By use of the appropriate differentiating agents one can influence what cells the precursor cells differentiate into. In standard culture conditions, the majority of precursor cells become hepatocytes.

The method of the present invention provides for deriving clonal lines of hepatocyte precursor cell lines by limiting dilution plating or single cell sorting under conditions which enhance guanine nucleotide biosynthesis, thereby suppressing asymmetric cell kinetics. In one preferred embodiment, the hepatocyte precursor cell lines are hepatocyte progenitor cells which can be expanded in vitro and express hepatocyte-specific characteristics, including metabolic activities. In another preferred embodiment, the hepatic stem cells are cholangiocyte precursor stem cells which can be expanded in vitro and express cholangiocyte-specific characteristics.

As used herein, hepatocyte precursor cells are sometimes referred to as hepatic precursor cells or liver stem cells or simply as stem cells. These precursor cells include hepatocyte progenitor cells, also known as hepatocyte stem cells, and cholangiocyte precursor cells, also known as cholangiocyte stem cells. Hepatocyte precursor cells give rise to hepatocytes and other hepatic cells, including cholangiocytes and stellate cells. As used herein, precursor cells and stem cells are used interchangeably. As used herein, somatic stem cells derived from adult tissues are sometimes referred to as somatic tissue stem cells or somatic stem cells or adult stem cells or simply as stem cells. As used herein, cholangiocytes are sometimes referred to as bile duct cells or biliary cells. As used herein, hepatic cells are a subpopulation of liver cells which include hepatocytes and cholangiocytes.

Suppression of Asymmetric Cell Kinetics

Adult somatic stem cells, including liver stem cells, predominantly divide by asymmetric cell kinetics. While somatic stem cells also undergo limited symmetric divisions (that produce two identical stem cells) in developing adult tissues, such symmetric kinetics are restricted to periods of tissue expansion and tissue repair. Inappropriate symmetric somatic stem cell divisions evoke mechanisms leading to apoptosis of duplicitous stem cells (Potten and Grant, 1998). Some stem cells may also lie dormant for long periods before initiating division in response to specific developmental cues, as in reproductive tissues like the breast. However, the predominant cell kinetics state of somatic stem cells is asymmetric (Cairns, 1975; Poldosky, 1993; Loeffler and Potten, 1997).

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transit cells (Loeffler and Potten, 1997). Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of stem cells and constant adult body mass. Mutations that disrupt asymmetric cell kinetics are an absolute requirement for the formation of a clinically significant tumor mass (Cairns, 1975). In many ways, asymmetric cell kinetics provide a critical protective mechanism against the emergence of neoplastic growths that are life threatening.

In culture, continued asymmetric cell kinetics of explanted cells are a major obstacle to their expansion in vitro (FIG. 1). Ongoing asymmetric kinetics results in dilution and loss of an initial relatively fixed number of stem cells by the accumulation of much greater numbers of their terminally differentiating progeny. If a sample includes both exponentially growing cells as well as somatic stem cells, the growth of the exponentially growing cells will rapidly overwhelm the somatic stem cells, leading to their dilution.

One regulator of asymmetric cell kinetics is the p53 tumor suppressor protein. Several stable cultured murine cell lines have been derived that exhibit asymmetric cell kinetics in response to controlled expression of the wild-type murine p53 (Sherley, 1991; Sherley et al, 1995 A-B; Liu et al., 1998 A-B; Rambhatla et al., 2001).

The p 53 model cell lines have been used to define cellular mechanisms that regulate asymmetric cell kinetics. In addition to p53, the rate-limiting enzyme of guanine nucleotide biosynthesis, inosine-5'-monophosphate dehydrogenase (IMPDH) is an important determinant of asymmetric cell kinetics. IMPDH catalyzes the conversion of IMP to xanthosine monophosphate (XMP) for guanine nucleotide biosynthesis. This enzymatic reaction is rate-determining for the formation of the next metabolite in the pathway, GMP, from which all other cellular guanine nucleotides are derived.

Accordingly, high levels of GNPs promote exponential kinetics, whereas low levels of GNPs promote asymmetric cell kinetics. The present invention provides methods for generating hepatic precursor cell lines which can be expanded by enhancing guanine nucleotide biosynthesis, thereby expanding cellular pools of GNPs and conditionally suppressing asymmetric cell kinetics.

Mechanisms which function downstream of the GNPs to regulate cell kinetics (i.e. asymmetric v. exponential) can also be used to conditionally suppress asymmetric cell kinetics. These mechanisms include both genetic and/or pharmacological approaches, analogous to those described in detail herein. For example, one can enhance expression of a protein downstream of the GNP biosynthesis pathway, if that protein inhibits asymmetric cell kinetics. Alternatively, one can downregulate expression of a protein downstream of the GNP pathway if it promotes asymmetric cell kinetics.

Isolation of Hepatic Precursor Cells

Hepatic precursor cells, also known as hepatocyte precursor cells, may be isolated from any available source using any available method. The isolation of hepatocyte precursor cells is known. See, e.g., U.S. Pat. No. 6,146,889, which is hereby incorporated by reference.

The present invention provides for the isolation of hepatic precursor cells from an animal cell population. Hepatic precursor cells include hepatocyte progenitor cells and cholangiocyte progenitor cells.

The cell population of hepatic precursor cells include hepatocyte progenitor cells, which contains immature cells (i) at least a portion of said cells or a portion of the progeny of said cells is capable of differentiating into hepatocytes and (ii) which are characterized by expression of alpha-fetoprotein or lack of essential expression of alpha-fetoprotein and albumin, and at least a portion of said cells or of the progeny of said cells is capable of differentiating into cells which express albumin. In general, the differentiated cells which express albumin have morphological and physiological characteristics of mature hepatocytes. As described below, the cell population has been cultured under conditions which result in expansion of the immature cells. Such cells are sometimes hereinafter referred to as "hepatocyte progenitors".

The cell population of hepatic precursor cells also includes cholangiocyte progenitor cells, which contains immature cells (i) at least a portion of said cells or a portion of the progeny of said cells is capable of differentiating into cholangiocytes, and (ii) which are characterized by expression of the bile duct marker cytokeratin 7, also known as CK7, and at least a portion of said cells or of the progeny of said cells is capable of producing tubular structures in culture under appropriate conditions.

The hepatic precursor cells may be derived from any animal, preferably from mammals, including but are not limited to humans, primates, rodents (e.g., rats, mice, hamsters), rabbits, bovines, horses, pigs, and sheep. Preferably, the hepatocyte precursors are derived from humans, pigs, and primates. More preferably, humans.

Although the hepatic precursor cells are preferably obtained from liver tissue, such cells may be obtained from other sources, including but not limited to the pancreas, gut, lung, and bone marrow. Hepatic precursor cells may also be isolated from embryonic tissue.

In general, hepatic precursor cells may be obtained from an excised section of liver. The excised section of liver may then be dissociated by standard procedures into single dissociated cells. Such procedures include enzymatic dissociation and mechanical dissociation. Enzymatic dissociation may be carried out in the presence of protease(s), such as collagenase(s) and/or nuclease(s), such as DNase. In some instances, pronase(s) may also be used. Such pronase(s) also contribute to the enrichment of hepatocyte precursor cells. An example of enzymatic dissociation of liver cells is described in Pretlow, et al., eds., Cell Separation: Methods and Selected Applications, pgs. 45-77, Academic Press, New York (1987). The cells are then subjected to an enrichment procedure to eliminate mature liver cells from the cell population. Procedures for enrichment include but are not limited to enzymatic digestion with pronase, DNase, and collagenase; centrifugal elutriation for cells which are smaller than mature hepatocytes; and freezing the cells in liquid nitrogen in the presence of 10% glycerol. It is to be understood, however, that the scope of the present invention is not to be limited to cells of a specific size range or a specific morphology. In one preferred embodiment, hepatocyte precursor cells are isolated from rat epithelial cells found in the low-speed supernatant of centrifuged cells from in situ collagenase-perfused livers.

Alternatively, the immature cells may be enriched by contacting cells from an excised section of liver tissue, or of other tissue, which may contain the hepatic precursor cells, with monoclonal antibodies which recognize an epitope of the hepatic precursor cells. Such cells may then be separated from the remainder of the cells of the excised tissue by procedures known to those skilled in the art.

One example of an enrichment procedure entails obtaining a liver section, and placing the liver section in an ice-cold saline solution which may contain buffers, glucose, and/or antibiotics. The liver section is then minced and sequentially digested with a solution containing collagenase, pronase, and deoxyribonuclease, prepared in a saline solution to which $CaCl_2$ is added. The digestions preferably are done at 37° C. in a shaking water bath and for a period of time of about 20 minutes. The partially digested tissue is then strained through a tissue sieve by gravity and the undigested remnants are redigested two times as herein described. The collected cells are then washed with saline solution, counted, and assessed for viability.

The enriched hepatic precursor population may be cultured under conditions which support the expansion or proliferation of the hepatic precursor cells, comprising culturing the immature cells in the presence of (i) an extracellular matrix and (ii) liver stromal cells. Preferably, the liver stromal cells are embryonic liver stromal cells or fetal liver stromal cells. In general, stromal cells are mesenchymally-derived cells that in vivo are closely associated with and are in a paracrine relationship with epithelia. Stromal cells also grow readily in culture on tissue culture plastic and in serum-supplemented media. In general, such cells also produce fibrillar collagens.

Examples of extracellular matrix components include, but are not limited to collagen, such as, for example, collagen Type IV, or the adhesion proteins fibronectin, and laminin. A preferred extracellular matrix component is collagen Type IV.

The collagen, when employed, may be used alone or in combination with laminin or fibronectin, or in combination with proteoglycans, or with tissue extracts enriched in extracellular matrix materials.

Preferably, the extracellular matrix component is coated upon a porous solid support. Examples of porous solid supports which may be employed include, but are not limited to porous supports such as Millicell membrane supports, filters, sponges, and hollow fiber systems. Alternatively, the extracellular matrix may be unattached to the porous solid support. Examples of such matrices include floating collagen gels, gel foams, spheres of synthetic materials or fibers of synthetic materials such as dextran, polystyrene, and agarose.

To generate cell lines, any method of clonal isolation of the hepatic precursor cells which does not generate neoplastically transformed cells may be used. A preferred method is limiting dilution plating, for example in 96-well plates, and limiting dilution cloning in peptide hydrogels. Methods for deriving clonal cell lines are well known in the art and are described for example in Puck et al., 1956; Nias et al., 1965; and Leong et al., 1985.

Pharmacological Methods for Generating and Expanding Hepatic Precursor Cell Lines In the pharmacological method of the present invention, hepatic precursor stem cells are isolated and cultivated in the presence of compounds which enhance guanine nucleotide biosynthesis. This expands guanine nucleotide pools, which in turn suppress the undesired asymmetric cell kinetics thereby permitting expansion of the hepatic precursor cells. Preferably, the compounds are guanine nucleotide precursors (rGNPrs). Even more preferably, the rGNPr is xanthosine (Xs) or hypoxanthine (Hx). More preferably, the rGNPr is xanthosine. These compounds can be used in effective amounts depending upon the culturing condition. Xanthosine can be used from 1-10,000 µM. Hypoxanthine can be used from 1-5000 µM. More specifically, xanthosine and hypoxanthine can be used from 50-400 µM. Further optimization of effective dosages can be determined empirically.

Genetic Methods for Generating and Expanding Hepatic Precursor Cell Lines

In another embodiment of the invention, genes that lead to constitutive upregulation of guanine ribonucleotides (rGNPs) are introduced into the isolated hepatic precursor cells. Preferred genes are those that encode inosine-5' monophosphate dehydrogenase (IMPDH) or xanthine phosphoribosyltransferase (XPRT), or other genes which have the same biochemical effect. More preferably, the gene is XPRT. While there are currently no known mammalian forms of XPRT, and its substrate xanthine is present in very low levels in mammalian cells, the activity of the transgenic XPRT can be regulated by supplying xanthine exogenously. As explained below, it is preferred that the genes are operably linked to an inducible promoter.

As used herein, the introduction of DNA into a host cell is referred to as transduction, sometimes also known as transfection or infection. Hepatic precursor cells can be transduced in vitro at high efficiency.

As used herein, the terms "transgene", "heterologous gene", "exogenous genetic material", "exogenous gene" and "nucleotide sequence encoding the gene" are used interchangeably and meant to refer to genomic DNA, cDNA, synthetic DNA and RNA, mRNA and antisense DNA and RNA which is introduced into the precursor cell. The exogenous genetic material may be heterologous or an additional copy or copies of genetic material normally found in the individual or animal. When cells are to be used as a component of a pharmaceutical composition in a method for treating human diseases, conditions or disorders, the exogenous genetic material that is used to transform the cells may also encode proteins selected as therapeutics used to treat the individual and/or to make the cells more amenable to transplantation.

An expression cassette can be created for expression of the gene that leads to constitutive upregulation of guanine ribonucleotides. Such an expression cassette can include regulatory elements such as a promoter, an initiation codon, a stop codon, and a polyadenylation signal. It is necessary that these elements be operable in the stem cells or in cells that arise from the stem cells after infusion into an individual. Moreover, it is necessary that these elements be operably linked to the nucleotide sequence that encodes the protein such that the nucleotide sequence can be expressed in the stem cells and thus the protein can be produced. Initiation codons and stop codons are generally considered to be part of a nucleotide sequence that encodes the protein.

A variety of promoters can be used for expression of the transgene. Preferably, the promoters are expressed at high levels in hepatocytes and hepatic precursor cells. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter and the herpes simplex tk virus promoter. For example, one can use a liver specific promoter, i.e. a promoter that functions in liver cells but not in others. Regulatable promoters are preferred. Such systems include those using the lac repressor from E. coli as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone or rapamycin [see Miller and Vvhelan, supra at FIG. 2]. Inducible systems are available from Invitrogen, Clontech and Arlad. Systems using a repressor with the operon are preferred. Regulation of transgene expression in target cells represents a critical aspect of gene therapy. For example, the lac repressor from Escherichia coli can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP16) to create a tetR-mammalian cell transcription activator fusion protein, tTa (tetR-VP16), with the tetO-bearing minimal promoter derived from the human cytomegalovirus (hCMV) major immediate-early promoter to create a tetR-tet operator system to control gene expression in mammalian cells. Recently Yao and colleagues [F. Yao et al., Human Gene Therapy, supra] demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells [M. Gossen et al., Natl. Acad. Sci. USA, 89:5547-5551 (1992); P.

Shockett et al., *Proc. Natl. Acad. Sci. USA,* 92:6522-6526 (1995)], to achieve its regulatable effects.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, given the large number of cells being used, preferably at least $1 \times 10^4$, more preferably at least $1 \times 10^5$, still more preferably at least $1 \times 10^6$, and even more preferably at least $1 \times 10^7$, the effect of silencing is minimal. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

In order to maximize protein production, codons may be selected which are most efficiently translated in the cell. The skilled artisan can prepare such sequences using known techniques based upon the present disclosure.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene. These marker genes can be under the control of any promoter or an inducible promoter. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

For example, one can set up systems to screen hepatic precursor cells automatically for the marker. In this way one can rapidly select transduced stem cells from non-transformed cells. For example, the resultant particles can be contacted with about one million cells. Even at transduction rates of 10-15% one will obtain 100-150,000 cells. An automatic sorter that screens and selects cells displaying the marker, e.g. GFP, can be used in the present method.

When the transgene is XPRT, cells expressing XPRT will be resistant to cytotoxic IMPDH inhibitors such as mycophenolic acid in the presence of xanthine. Thus, transduced stem cells can be selected from non-transformed cells by culturing transfectants in the presence of an IMPDH inhibitor (such as mycophenolic acid) and xanthine.

Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Preferred vectors include viral vectors, fusion proteins and chemical conjugates. Retroviral vectors include Moloney murine leukemia viruses and pseudotyped lentiviral vectors such as FIV or HIV cores with a heterologous envelope. Other vectors include pox vectors such as orthopox or avipox vectors, herpesvirus vectors such as a herpes simplex I virus (HSV) vector (Geller, A. I. et al., (1995), *J. Neurochem,* 64: 487; Lim, F., et al., (1995) in *DNA Cloning: Mammalian Systems,* D. Glover, Ed., Oxford Univ. Press, Oxford England; Geller, A. I. et al. (1993), *Proc Natl. Acad. Sci.:* U.S.A. 90:7603; Geller, A. I., et al., (1990) *Proc Natl. Acad. Sci USA* 87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The introduction of the gene into the hepatic precursor cell can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters, etc.

The vectors are used to transduce the hepatic precursor cells ex vivo. One can rapidly select the transduced cells by screening for the marker. Thereafter, one can take the transduced cells and grow them under the appropriate conditions or insert those cells into a host animal.

Somatic Tissue Stem Cells

The hepatic precursor cells produce daughter cells that mature into differentiated cells under specific conditions. The hepatic precursor cells can be isolated from the individual in need of stem cell therapy or from another individual. Preferably, the individual is a matched individual to insure that rejection problems do not occur. Therapies to avoid rejection of foreign cells are known in the art. Furthermore, hepatic precursor cells may be immune-privileged, so the graft versus host disease after allogenic transplant may be minimal or non-existent (Weissman, 2000). Endogenous or stem cells from a matched donor may be administered by any known means, preferably intravenous injection, or injection directly into the liver or other appropriate tissue.

As stated above, hepatic precursor cells may also be derived from the individual to be treated or a matched donor. Those having ordinary skill in the art can readily identify matched donors using standard techniques and criteria.

Cells can be obtained from donor tissue by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument.

Dissociation of cells can be carried out in any acceptable medium, including tissue culture medium. The dissociated stem cells can be placed into any known culture medium capable of supporting cell growth, including DMEM, RPMI, HEM, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds which enhance guanine nucleotide biosynthesis, although generally at levels below the effective concentration to suppress asymmetric cell kinetics. Thus, preferably a defined, serum-free culture medium is used, as serum contains unknown components (i.e. is undefined). Preferably, if serum is used, it has been dialyzed to remove rGNPrs. A defined culture medium is also preferred if the cells are to be used for transplantation purposes. A particularly preferable culture medium is a defined culture medium comprising a mixture of DMEM, F12, and a defined hormone and salt mixture. As indicated herein, by including a compound such as a rGNPr, asymmetric cell kinetics are suppressed. Thus, the effect of division by differentiated transit cells, which results in the diluting of the stem cells, is reduced.

The culture medium can be supplemented with a proliferation-inducing growth factor(s). As used herein, the term "growth factor" refers to a protein, peptide or other molecule having a growth, proliferative, differentiative, or trophic effect on hepatic precursor cells and/or hepatic precursor cell progeny. Growth factors that may be used include any trophic factor that allows stem cells to proliferate, including any molecule that binds to a receptor on the surface of the cell to exert a trophic, or growth-inducing effect on the cell. Preferred proliferation-inducing growth factors include EGF, amphiregulin, acidic fibroblast growth factor ($\alpha$FGF or FGF-1), basic fibroblast growth factor ($\beta$FGF or FGF-2), transforming growth factor alpha (TGF$\alpha$), and combinations thereof. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGF$\beta$s), insulin-like growth factor (IGF-1) and the like.

Hepatic precursor cells can be cultured in suspension or on a fixed substrate. One particularly preferred substrate is a hydrogel, such as a peptide hydrogel, as described below and in U.S. Ser. No. 09/778,200 and U.S. Ser. No. 60/305,379, which are hereby incorporated by reference. However, certain substrates tend to induce differentiation of certain stem cells. Thus, suspension cultures are preferable for such stem cell populations. Cell suspensions can be seeded in any receptacle capable of sustaining cells, particularly culture flasks, cultures plates, or roller bottles, more particularly in small culture flasks such as 25 cm$^2$ cultures flasks. In one preferred embodiment, cells are cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Uses of Hepatic Precursor Cells

The present invention also provides for the administration of expanded populations of hepatic precursor cells to a patient in need thereof. The expanded stem cells of the present invention can be used for a variety of purposes, including but not limited to liver cell (hepatic) transplants, gene therapies, tissue engineering, development of a bioartificial liver, and in vitro organogenesis. Production of autologous stem cells to replace injured tissue would also reduce the need for immune suppression interventions.

Gene Therapy Applications

According to the invention, in addition to the introduction of genes that lead to constitutive upregulation of guanine ribonucleotides, the hepatic precursor cells can be further genetically altered prior to reintroducing the cells into the individual for gene therapy, to introduce a gene whose expression has therapeutic effect on the individual.

In some aspects of the invention, individuals can be treated by supplementing, augmenting and/or replacing defective and/or damaged cells with cells that express a therapeutic gene. The cells may be derived from hepatic precursor cells of a normal matched donor or stem cells from the individual to be treated (i.e., autologous). By introducing normal genes in expressible form, individuals suffering from such a deficiency can be provided the means to compensate for genetic defects and eliminate, alleviate or reduce some or all of the symptoms.

A vector can be used for expression of the transgene encoding a desired wild type hormone or a gene encoding a desired mutant hormone. Preferably, as described above, the transgene is operably linked to regulatory sequences required to achieve expression of the gene in the stem cell or the cells that arise from the stem cells after they are infused into an individual. Such regulatory sequences include a promoter and a polyadenylation signal. The vector can contain any additional features compatible with expression in stem cells or their progeny, including for example selectable markers.

In another preferred embodiment, the transgene can be designed to induce selective cell death of the stem cells in certain contexts. In one example, the stem cells can be provided with a "killer gene" under the control of a liver-specific promoter such that any stem cells which differentiate into cell types other than liver cells will be selectively destroyed. In this example, the killer gene would be under the control of a promoter whose expression did not overlap with the liver-specific promoter.

Alternatively, the killer gene is under the control of an inducible promoter that would ensure that the killer gene is silent in patients unless the gene therapy is to be stopped. To stop the therapy, a pharmacological agent is added that induces expression of the killer gene, resulting in the death of all cells derived from the initial stem cells.

In another embodiment, the stem cells are provided with genes that encode a receptor that can be specifically targeted with a cytotoxic agent. An expressible form of a gene that can be used to induce selective cell death can be introduced into the cells. In such a system, cells expressing the protein encoded by the gene are susceptible to targeted killing under specific conditions or in the presence or absence of specific agents. For example, an expressible form of a herpes virus thymidine kinase (herpes tk) gene can be introduced into the cells and used to induce selective cell death. When the exogenous genetic material that includes (herpes tk) gene is introduced into the individual, herpes tk will be produced. If it is desirable or necessary to kill the transplanted cells, the drug ganciclovir can be administered to the individual and that drug will cause the selective killing of any cell producing herpes tk. Thus, a system can be provided which allows for the selective destruction of transplanted cells.

Administration of Expanded Hepatic Precursor Cells

This method involves administering by standard means, such as intravenous infusion or mucosal injection, the expanded hepatic precursor cells to a patient.

The discovery that isolated hepatic precursor cells may be expanded ex vivo and administered intravenously provides the means for systemic administration. Intravenous administration also affords ease, convenience and comfort at higher levels than other modes of administration. In certain applications, systemic administration by intravenous infusion is more effective overall.

After isolating the hepatic precursor cells, the cells can be administered after a period of time sufficient to allow them to convert from asymmetric cell kinetics to exponential kinetics, typically after they have been cultured from 1 day to over a year. Preferably the cells are cultured for 3-30 days, more preferably 4-14 days, most preferably at least 7 days.

In one embodiment of the invention, the hepatic precursor cells can be induced to differentiate following expansion in vitro, prior to administration to the individual. Preferably, the pool of guanine ribonucleotides is decreased at the same time differentiation is induced, for example by removal of the rGNPr from the culture medium (if a pharmacological approach has been used) or by downregulating expression of the transgene.

Differentiation of the hepatic precursor cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, MATRIGEL™ (Collaborative Research), and the like. Differentiation can also be induced by leaving the cells in suspension in the presence of a proliferation-suppressing growth factor, without reinitiation of proliferation.

Differentiation can be determined using immunocytochemistry techniques well known in the art. Immunocytochemistry (e.g. dual-label immunofluorescence and immunoperoxidase methods) utilizes antibodies that detect cell proteins to distinguish the cellular characteristics or phenotypic properties of differentiated cell types compared to markers present on hepatic precursor cells.

For administration of hepatic precursor cells, the isolated stem cells are removed from culture dishes, washed with saline, centrifuged to a pellet and resuspended in a glucose solution which is infused into the patient.

Between $10^5$ and $10^{13}$ cells per 100 kg person are administered per infusion. Preferably, between about $1-5 \times 10^8$ and $1-5 \times 10^{12}$ cells are infused intravenously per 100 kg person. More preferably, between about $1 \times 10^9$ and $5 \times 10^{11}$ cells are infused intravenously per 100 kg person. For example, dosages such as $4 \times 10^9$ cells per 100 kg person and $2 \times 10^{11}$ cells can be infused per 100 kg person. The cells can also be injected directly into the liver.

In some embodiments, a single administration of cells is provided. In other embodiments, multiple administrations are used. Multiple administrations can be provided over periodic time periods such as an initial treatment regime of 3-7 consecutive days, and then repeated at other times.

The term "animal" here denotes all mammalian animals except humans. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

EXAMPLE 1

Clonal Expansion of Adult Rat Hepatic Stem Cell Lines by Suppression of Asymmetric Cell Kinetics (SACK)

Materials and Methods

Materials

With the exception of anti-albumin (EY Laboratories) and anti-CK7 (Chemicon) antibodies, all specific antibodies for immunoblotting studies were supplied by Santa Cruz. D. Hixon (Brown University, Providence, R.I.) kindly provided anti-H.4 antibodies. Xanthosine (Xs) was purchased from Sigma Chemical Co. (St. Louis, Mo.). Other antibodies used in immunohistochemical studies were supplied by Serotec.

SACK Cell Line Derivation and Culture

The starting cell preparation for SACK derivation was the non-parenchymal (NPC) cell fraction from male Fischer 344 rats prepared by in situ collagenase perfusion as described by others (Michalopoulos et al., 1999). The NPC cell fraction was centrifuge at 800 g for 5 minutes at 4° C. The resulting cell pellet was re-suspended in 30 ml of DMEM (high glucose, 4.5 mg/ml) supplemented with 10% dialyzed fetal bovine serum (dFBS, JRH Biosciences). The cells were then pelleted at 200 g for 5 minutes at 4° C. After re-suspension in 30 ml of medium, 20 ml of the cell suspension ($10^7$ viable cells) were placed into two 75-cm² culture flasks (10 ml each) and incubated overnight at 37° C. in a humidified incubator with a 5% $CO_2$ atmosphere.

Adherent cells in the two flasks were removed with trypsin, combined into 20 ml of the medium, and pelleted at 200 g for 5 minutes at 4° C. The cells were then re-suspended in 20 ml of medium, and the viable cell number determined by trypan blue exclusion. Cells were diluted to a density of 20 viable cells per ml in the same culture medium containing either 200 µM or 400 µM Xs. Aliquots of 100 µl of the diluted cells were pipetted into 96-well culture plates (i.e., giving an expected average of 2 cells per well).

After two weeks of culture in 96-well plates, wells with single epithelioid cell colonies were identified by phase microscopy. The culture medium was aspirated from these wells; the cells were washed briefly with 0.2 ml phosphate-buffered saline; and 50 µl of Cell Dissociation Solution (Sigma Cat. #C5914) was added. After a 5-minute incubation at 37° C. in a humidified incubator with a 5% $CO_2$ atmosphere, 0.2 ml of the respective Xs-containing medium was added. The cells were gently dissociated with a 1-ml micropipet and then transferred to one well of a 24-well culture plate containing 5 ml of Xs-containing medium.

The culture medium was changed the next day after transfer and thereafter every 2 days until wells were 20-80% confluent. This medium change protocol was followed after all culture transfers. Subsequently, ½-standard strength trypsin was used to transfer cells sequentially from 6-well plates, to 25-cm² culture flasks, and finally to 75-cm² culture flasks. After reaching the 75-cm² stage, cells were maintained in normal Xs-containing medium with 1:3 splits when they reached 80% confluency. Thereafter, for routine culture, all cell lines were maintain with 1:20 to 1:5 splits when they reached ≧80% confluency. The procedure for conventionally derived lines (Lig-1, -2, and -3) was the same as for Xs-derived lines, except Xs-free medium was used throughout.

For soft agar studies, cells were plated at a density of $1\times10^5$ per 2 ml of 0.3% agarose in culture medium. This volume was added to wells of a 6-well culture plate containing a 3 ml layer or 0.5% agarose in culture medium as described (Clarke et al., 2002).

Early passage cells were cryo-preserved by re-suspension in 70% DMEM (high glucose)/20% fetal bovine serum/10% DMSO. The cells from an 80% confluent 75-cm$^2$ culture flask were re-suspended in 4.5 ml of freezing medium and frozen as 1.5-ml aliquots. Cell suspensions were placed in a Styrofoam box at −80° C. overnight and then transferred to liquid nitrogen for long-term preservation.

Fc(t) Analysis

To initiate the assay, 100 cells were plated in 75-cm$^2$ flasks. After a 16-hour growth period, pairs of new daughter cells were identified under the microscope, and their positions marked for serial examination. Thereafter, the marked microcolonies were examined at roughly ⅓ GT intervals for at least 2 generations. At each examination, the fraction of cells that divided during the previous interval was calculated as described (Sherley et al., 1995a). The estimated cell GT of examined lines was determined simultaneously as described (Sherley et al., 1995ab).

Daughter Pair Analysis (DPA)

Into 10-cm diameter culture dishes, an estimated 1750 cells were plated in DMEM-10% dFBS, supplemented at the Xs concentration used for derivation, and cultured for 16 hours. Medium was then replaced with either Xs-free medium or medium containing 100 µM Xs, and cells were cultured for an additional 48 h (GT=60 h). Bromo-5-deoxyuridine (BrdU) was then added to the cultures to a concentration of 5 µM for 5 hours. Detection of incorporated BrdU was performed using primary antibody Bu1-75 (Harlan), and a biotinylated secondary antibody (Vector Laboratories) with avidin-fluorescein visualization. Nuclei were detected by staining with 0.5 µg/ml DAPI (Molecular Probes). Images were captured using a Nikon TE300 microscope, Orca camera, and Openlab software (Improvision).

Lineage-Specific Marker Expression Analyses

For serum protein secretion analyses, cells were grown to confluency in maintenance medium over 4 days. On the fifth day, cell monolayers were washed twice in phosphate-buffered saline (PBS). Serum-free medium was added, and a 0.5-ml sample of medium was immediately withdrawn ("0 h"). Cells were returned to the incubator, and 0.5-ml samples of medium were collected at 24 h, 48 h, and 72 h. At each collection, the medium sample was centrifuged at low speed (6000 rpm in an Eppendorf™ microfuge for 10 minutes) to pellet any cells present without breaking them. The supernatant was stored at −70° C. until further analysis.

To prepare cell lysates, cells were cultured until 95% confluent. After washing once with ice cold PBS, the cells were solubilized on ice in ice-cold lysis buffer (RIPA buffer; Hinds et al., 1987). The cell lysates were clarified by centrifugation at 13,000 rpm (Eppendorf™ microfuge) for 30 minutes at 4° C. and stored at −70° C. until further analysis. Soluble protein in lysates was quantified using the Bio-Rad DC™ assay.

Twenty micrograms of cell lysates or 25 µl of culture medium samples were separated by SDS-PAGE (8-12% polyacrylamide) and analyzed for specific proteins by the following immunoblot procedure. Electrophoresed proteins were transferred to Hybond ECL membranes in Tris-Glycine-Methanol buffer (25 mM Tris-HCl, pH 7.5, 190 mM glycine, 20% methanol) for 1 hour at 100 volts at room temperature. Membranes were then stained with Ponceau S (0.5%) to verify uniform protein transfer and then blocked with Tris-buffered saline, 5% non-fat dried milk, 0.1% Tween-20 at room temperature for 1 hour. Following three 10-minute washes at room temperature in Tris-buffered saline, 0.1% Tween-20, the membranes were incubated with the specific primary antibodies diluted appropriately in Tris-buffered saline, 1% milk, 0.1% Tween-20 for 12-15 hours at 4° C. For albumin detection, membranes were incubated with an anti-albumin-HRP antibody (EY Laboratories) for 1 hour at room temperature. After removal of the unbound antibodies with three 10-minute washes in Tris-buffered saline-0.1% Tween-20, the membranes (except for albumin detection) were incubated with the anti-goat-HRP (1:2000) or anti-mouse HRP (1:5000) for 1 hour at room temperature. After three 10-minute washes with Tris-buffered saline-0.1% Tween-20, specifically bound HRP-conjugated antibodies were detected using the Amersham Enhanced Chemiluminescence Plus™ system. To re-probe a membrane with a different antibody, it was first incubated for 2.5 h in 0.1M glycine (pH 2.5) at room temperature.

Immunohistochemical staining was performed with HRP-conjugated secondary antibodies as recommended by the supplier of primary detection antibodies.

EROD Assay

Cultures were incubated with 7-ethoxyresorufin (400 nM) and dicumoral (10 µM) in maintenance growth medium for one hour. Culture supernatant samples were analyzed at 571-nm excitation, 585 emission, and quantified by comparison to a resorufin standard curve.

Results

SACK-Derived Adult Rat Hepatic Epithelial Cell Lines Exhibit Xs-Dependent Cell Kinetics To derive "Lig" cell lines, cells in the low-g supernatant of centrifuged cell preparations from in situ collagenase-perfused livers were cloned by limiting dilution culture in the absence ("conventional") or presence of Xs ("Xs-derived or SACK-derived"). Colonies with epitheloid morphology arose with similar efficiency in both conditions (4.1±0.31%). The efficiency of establishing cell cultures from colonies was also similar, 50% (3/6) for conventional colonies and 65% (11/17) for Xs-derived. A total of 3 and 8, respectively, conventional and Xs-derived cell lines were derived. Each line has been maintained continuously in culture for >80 cell doublings and efficiently cryo-preserved at early and late passages.

There was a marked difference in the cell kinetics properties of early passage conventional lines (Lig-1 to -3 in Table 1) and Xs-derived lines (Lig-4 to -15 in Table 1). In Xs-free medium, as a group (n=8), Xs-derived lines exhibited a mean colony formation efficiency that was 85% less than the efficiency of conventional lines (p=0.004; Table 1, Xs−). However, in Xs-supplemented medium, the mean efficiency of Xs-derived lines was not significantly different than that of conventional lines (Table 1, Xs+). The estimated mean increase in colony formation efficiency for Xs-derived cell lines in Xs-supplemented medium was 11-fold (n=8), ranging from a 10% increase to a 40-fold increase (Lig-13 in Table 1; p<0.0001). The growth of conventional cell lines was unaffected by Xs even when the Xs concentration was doubled (data not shown).

The cell kinetics of Xs-derived lines were also density-dependent as previously described for asymmetric cell kinetics (Rambhatla et al., 2001). For example, Lig-9 cells showed the highest Xs-free colony formation efficiency among Xs-derived lines and no Xs-dependence when plated at 200 cells/19 cm$^2$. However, when plated at a 10-fold lower density (see Table 2B) they divided with asymmetric cell kinetics. In a related fashion, when Xs-derived cells were plated at a 3-fold higher density than that used for colony formation analyses or grown at cell densities used for routine maintenance, they grew exponentially even in the absence of Xs (data not shown). Thus, the most significant role of Xs may be in promoting exponential expansion until a critical cell density is reached, beyond which the Xs effect is diminished.

In only one case did the decreased growth of Xs-derived cells in Xs-free medium appear to be due to cell death (see Lig-7 in Table 1). After 2 weeks of culture in the absence of Xs, compared to Xs-supplemented cells, lines Lig-8, -13, and -15 show a significant reduction in colonies detected by visual inspection after staining with crystal violet. However, when these same wells are examined by microscopy, a similar number of crystal violet-positive (i.e., viable) colonies are observed. The difference in colony number is due to the presence of micro-colonies with less than 20 cells that are not detected by visual inspection with the naked eye. Micro-colonies of this type are consistent with the presence of asymmetric kinetics (Liu et al., 1998b; Sherley et al., 1995ab). Since no micro-colonies are found in Xs-free cultures of Lig-7 cells, it is likely that these cells die in the absence of Xs. This phenotype may indicate a cell variant with a defect in IMPDH, which is essential for growth, or a related function in guanine nucleotide metabolism.

Asymmetric Cell Kinetics by SACK-Derived Adult Rat Hepatic Epithelial Cell Lines A previously described serial colony formation analyses (the "Fc[t] assay"; Sherley et al., 1995a) was used to quantify the degree of asymmetric cell kinetics by Xs-derived cell lines. The Fc(t) assay quantifies the accumulation rate of cells in micro-colonies examined by serial phase microscopy at intervals of less than one GT from the 2-cell stage (Sherley et al., 1995a). Fc(t) is calculated by summing the fractions of dividing cells determined in each interval and dividing by the total number of GTs examined. When cells divide with symmetric kinetics, the value of Fc(t) approaches 1.0, regardless of the length of the examination period. For asymmetric kinetics, in which one non-dividing daughter is produced at each cell division, Fc(t) is a declining function that approaches 0.0 with increasing exam time. Its values after 2 and 3 GTs are 0.42 and 0.36, respectively.

The mean GT for individual dividing cells of all examined cell lines, in Xs-free or Xs-supplemented media, was remarkably similar at approximately 60 hours (determined as described in Sherley et al., 1995ab). This time was equivalent to the population doubling time (DT) of conventional cell lines determined by growth curve analyses in Xs-free medium at low cell density. The equivalence of GT and DT is indicative of exponential kinetics (Rambhatla et al., 2001; Sherley et al., 1995ab).

Fc(t) was determined for 2 GT periods for conventional and Xs-derived cell lines cultured in Xs-free medium (Table 2A). The first difference noted in these analyses was that Xs-derived lines had a significantly higher fraction of non-dividing daughter cell pairs (range 0.58 to 0.92; see Table 2, "terminal division fraction") compared to conventional lines (range 0.12 to 0.39). Some terminal divisions may occur for reasons other than asymmetric kinetics. However, finding that Xs-derived lines exhibit a 2.7-fold higher mean fraction of these divisions is consistent with the production of terminal transit cell lineages by asymmetric cell kinetics programs (Rambhatla et al., 2001).

Since Fc(t) analysis requires dividing micro-colonies, the high fraction of terminal divisions by Xs-derived cell lines limited their analysis by this method. Therefore, we compared combined Fc(t) determinations for conventional lines to those of Xs-derived lines. As shown in Table 2A, in Xs-free medium, conventional cell lines had a mean Fc(t) consistent with symmetric kinetics (p=0.035 for 0.73 different than the ideal asymmetric kinetics value 0.42). In contrast, Xs-derived lines had a mean Fc(t) consistent with asymmetric cell kinetics (p=0.473 for 0.51 different than the ideal asymmetric cell kinetics value 0.42).

Xs-Dependent Asymmetric Cell Kinetics by SACK-Derived Adult Rat Hepatic Epithelial Cell Lines Sufficient dividing micro-colonies were evaluated for an individual Fc(t) analysis for Xs-derived Lig-9 cells. Although Lig-9 cells showed no significant change in cell kinetics in response to Xs in colony formation experiments (Table 1), we noted that in Xs-supplemented medium Lig-9 colonies appeared denser, suggesting more cells (data not shown). At the reduced cell density required for Fc(t) analyses (1 per $cm^2$), Lig-9 cells exhibited a marked asymmetric cell kinetics phenotype (Table 2B). With Xs, Lig-9 cells had a mean Fc(t) value of 1.1, indicative of symmetric kinetics. In the absence of Xs, the mean value is 0.45, very near 0.42, the ideal value for asymmetric cell kinetics. It is noteworthy that Xs did not significantly affect the terminal division fraction of Lig-9 cells (Table 2B). This finding was consistent with the idea that Xs changed the symmetry of Lig-9 cell kinetics, but, at the concentrations used in these experiments (100 μM), it did not entirely suppressed the formation of terminally-arrested cells.

Two Xs-derived cell lines were selected for evaluation with a more sensitive assay for asymmetric cell kinetics. In colony formation studies, line Lig-8 exhibited the best combination of Xs-free growth and Xs-dependent cell kinetics, and line Lig-13 had the overall greatest dependence on Xs for growth (see Table 1). An in situ cytometry assay was used to directly visualize asymmetric daughter cells. The assay is based on the observation that cultured cells that model asymmetric cell kinetics produce non-dividing daughters that arrest prior to initiation of S phase DNA synthesis (Liu et al., 1998b; Sherley et al., 1995a).

The assay is called a "daughter pair analysis" (DPA). To perform the DPA, cells were plated in Xs-containing medium at microcolony density. After allowing 4 to 5 hours for cell adherence, parallel cultures were replaced with fresh medium that was either Xs-supplemented or Xs-free. After allowing time for cell divisions to produce "daughter pairs", the cells were cultured for 4 hours with the thymidine analogue bromodeoxyuridine (BrdU). Cells were then fixed and evaluated for BrdU incorporation by in situ immunofluorescence. FIG. 2 shows examples of results for Xs-derived line Lig-8 and conventional line Lig-1.

Figure 2C:
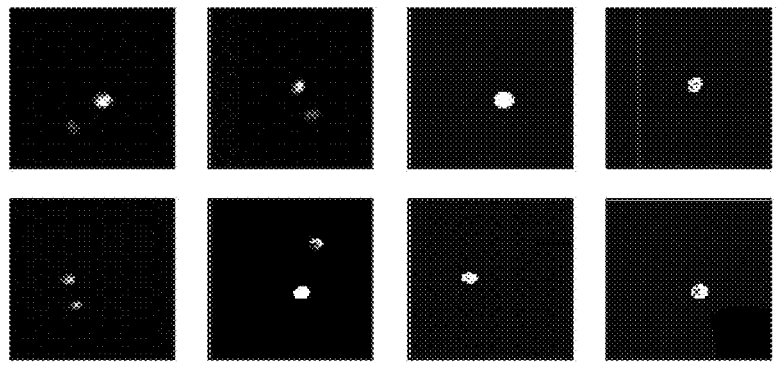
FIGS. 2A-2C show the detection of Xs-dependent asymmetric cell kinetics by Xs-derived Lig-8 cells using daughter pair analysis (DPA). Shown are examples of DPA images for paired newly-divided daughter cells for conventional Lig-1 cells cultured in the absence of Xs (FIGS. 2A and 2a), Xs-derived Lig-8 cells cultured in the presence of Xs (FIGS. 2B and 2b), and Lig-8 cells cultured in the absence of Xs (FIGS. 2C and 2c).
Figure 2B:
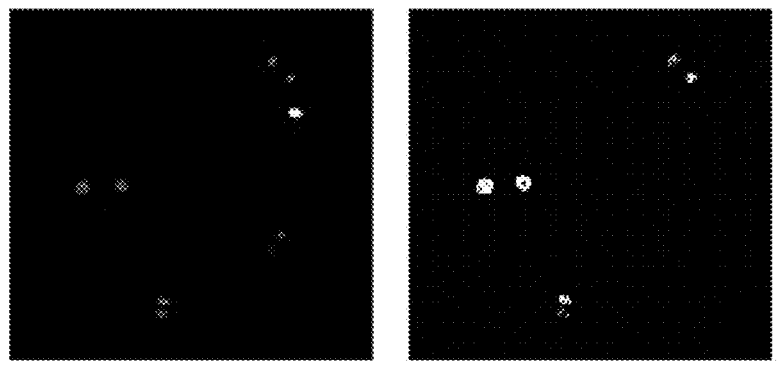
Figure 2A:
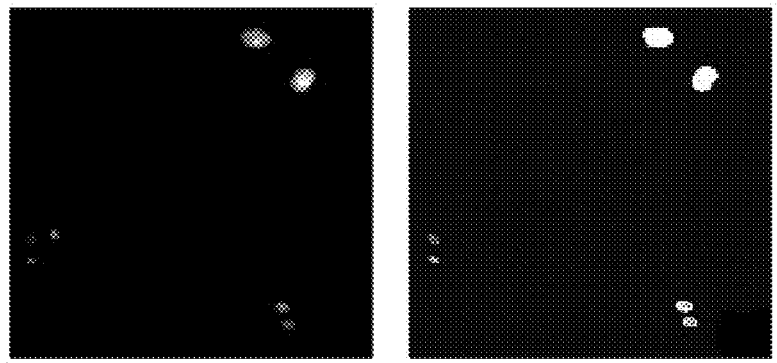

When grown in the absence of Xs, 84% of Lig-8 BrdU(+) daughter pairs showed a single BrdU(+) daughter (n=76 pairs; e.g., FIG. 2Cc). The BrdU(+) daughter is a cycling stem cell-like daughter, whereas the BrdU(−) daughter corresponds to an arrested transit cell-like daughter. Consistent with the ability of Xs to shift cells from asymmetric to symmetric cell kinetics, its addition increased the fraction of double-BrdU(+) Lig-8 daughter pairs from 16% to 76% (n=58 pairs; e.g., FIG. 2Bb). In contrast to Xs-derived Lig-8 cells, the majority of conventional Lig-1 BrdU(+) daughter pairs in Xs-free medium were symmetric (FIG. 2Aa), consistent with Xs-independent exponential cell kinetics. However, a significant fraction (39%) of asymmetric daughter pairs, with a single BrdU(+) daughter, was observed in Lig-1 cultures as well. Even so, for 70 scored daughter pairs in Xs-free medium, the frequency of Lig-1 symmetric pairs was 5 times the frequency of Lig-8 symmetric pairs. Unlike Lig-8 cells, Lig-13 cells showed the same high fraction of symmetric BrdU(+) daughter pairs (76%), independent of Xs concentration. This fraction was in fact higher than that observed for Lig-1 cells (61%).

Figure 3:
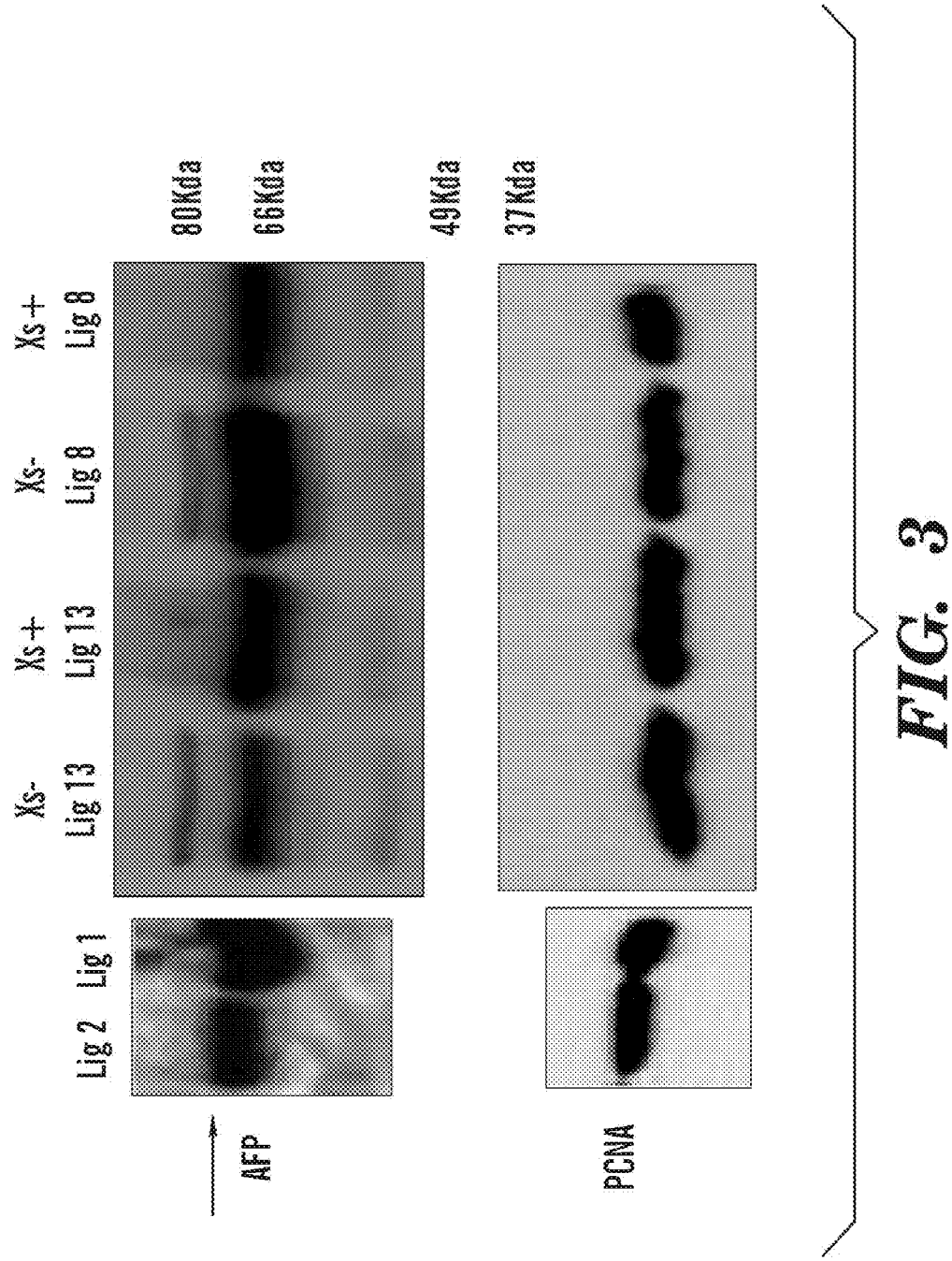
FIG. 3 shows immunoblot analysis of AFP expression in conventional and Xs-derived adult hepatic epithelial cell lines. Immunoblot analyses were performed to detect AFP in whole cell lysates (20 µg protein each) from conventional (Lig-1 and Lig-2) and Xs-derived (Lig-8 and Lig-13) cell lines. The membrane was re-probed with anti-proliferating cell nuclear antigen (PCNA) antibodies to verify extract loading. Xs-derived cells were cultured in Xs-free (Xs−) or Xs-supplemented medium (Xs+). Arrow indicates new 80 Kda anti-AFP-reactive protein detected in both Xs-derived lines when cultured in Xs-free medium.

Expression of Markers of Hepatocyte Cell Differentiation by SACK-Derived Cell Lines We next evaluated the differentiation properties of conventional and Xs-derived cell lines by examining expression of hepatic lineage-specific markers. The results of these studies are summarized in Table 3. None of the examined lines expressed markers evaluated for Kupffer cells or stellate cells. Both conventional lines and Xs-derived lines expressed similar levels of α-fetoprotein (AFP), a marker of embryonic hepatoblasts (Zaret, 1996; FIG. 3). The amount of AFP expression was similar for all examined lines. Interestingly, when cultured under Xs-free conditions, Xs-derived lines Lig-8 and Lig-13 cells expressed a new 80 kilodalton anti-AFP reactive protein (see FIG. 3, arrow). This protein was not detected in conventional Lig-1 and Lig-2 cells. The molecular basis for this species is unclear, but it may reflect a difference in AFP glycosylation (Young and Tilghman, 1986).

Figures 4A, 4B:
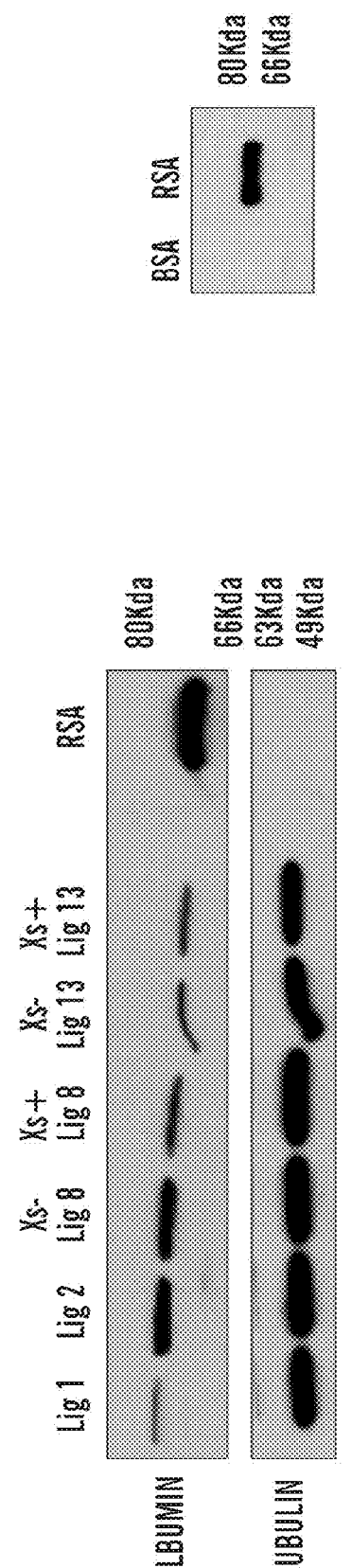
FIG. 4A: Immunoblot analysis of albumin in whole cell lysates (20 µg protein each) from conventional (Lig-1 and Lig-2) and Xs-derived (Lig-8 and Lig-13) cell lines. The membrane was re-probed with anti-β-tubulin antibodies to verify extract loading. Xs-derived cells were cultured in Xs-free (Xs−) or Xs-supplemented medium (Xs+). RSA, 50 nanograms purified rat serum albumin.
FIG. 4B: 50 nanograms each of purified bovine serum albumin (BSA) and rat serum albumin (RSA) were immunoblotted to insure that no significant cross-reactivity occurred with BSA derived from the cell culture medium. Lysates from murine fibroblasts grown in BSA-supplemented medium also showed no detectable albumin (data not shown).

All examined cell lines also expressed albumin, a marker of both embryonic hepatoblasts and mature hepatocytes (Grisham and Thorgeirsson, 1997). Albumin expression levels showed significant variation among cell lines (FIG. 4). Whereas Lig-8 cells and Lig-13 cells expressed similar albumin levels in Xs-supplemented medium, Lig-8 showed increased expression in Xs-free medium. Lig-13 albumin expression did not vary with Xs concentration.

Figure 5A:
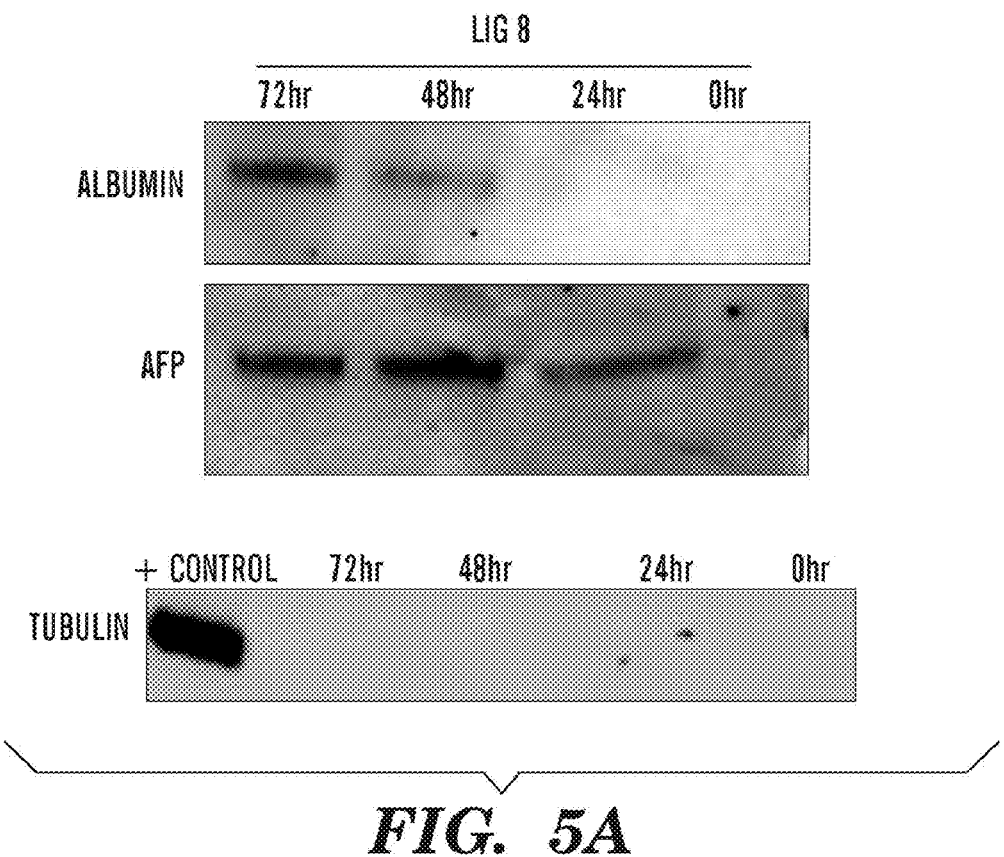
FIGS. 5A and 5B show immunoblot analysis of serum protein secretion by conventional and Xs-derived adult hepatic epithelial cell lines. Culture supernatants were collected at the indicated times after the medium of conventional (Lig-1 and Lig-2) and Xs-derived (Lig-8 and Lig-13) was replaced with serum-free medium as described in *Materials and Methods*.
Figure 5B:
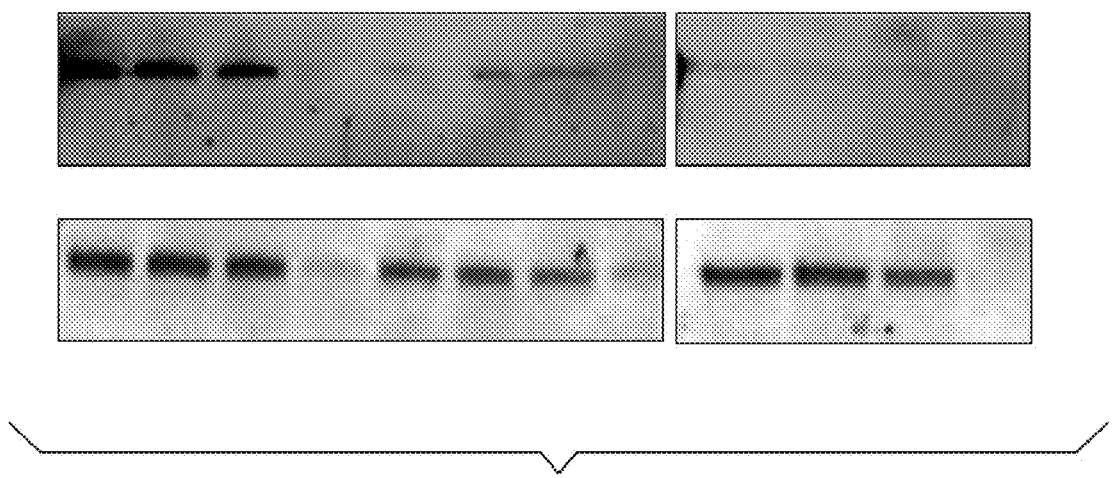

AFP and albumin are members of a small multi-gene family of serum proteins secreted by hepatocytes. AFP predominates in embryonic and fetal hepatocytes, but is replaced by albumin later in development (Grisham and Thorgeirsson, 1997). All examined cell lines secreted AFP with similar efficiency (FIGS. 5 A and B). In contrast, with one exception, albumin secretion matched the observed variation in albumin expression levels (Compare FIG. 4 data to FIG. 5). Although Lig-13 cells expressed 75% of the Lig-8 albumin level in Xs-supplemented medium (FIG. 3), they showed no detectable albumin expression (FIG. 5B). On the other hand, Lig-8 cells showed a significant level of albumin secretion (FIG. 5A; estimated 0.3 picogram/cell/day).

Figure 6A:
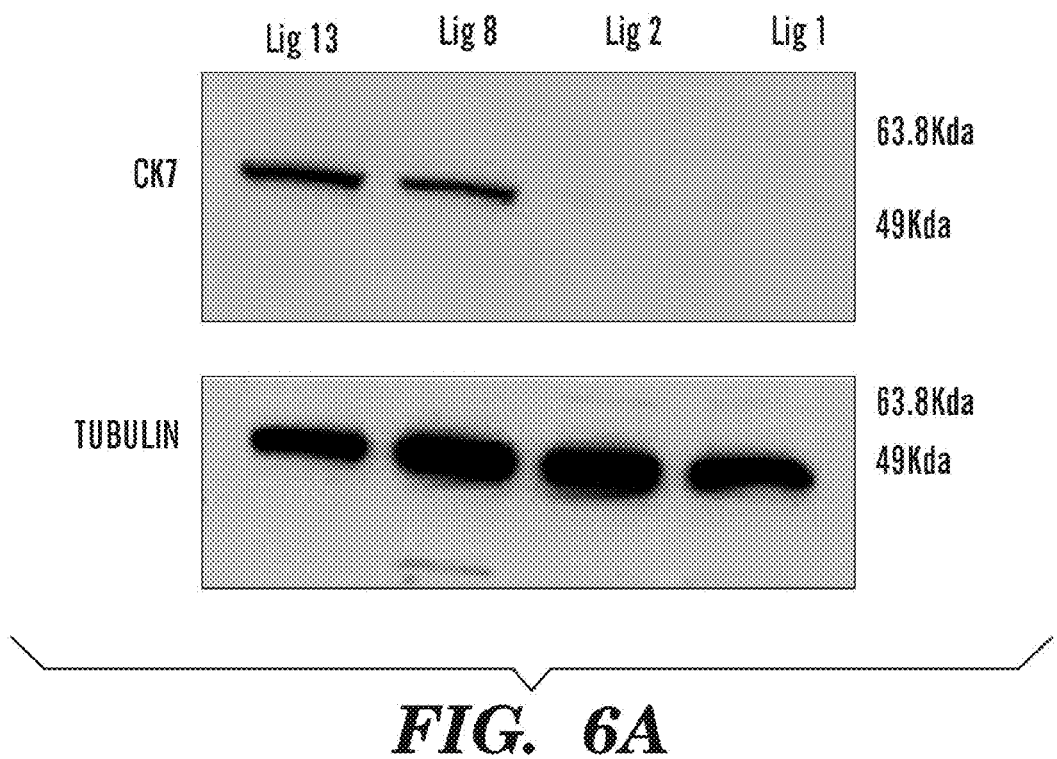
FIGS. 6A and 6B show immunoblot analysis of expression of markers of mature epithelial cell differentiation by conventional and Xs-derived adult hepatic cell lines.
Figure 6B:
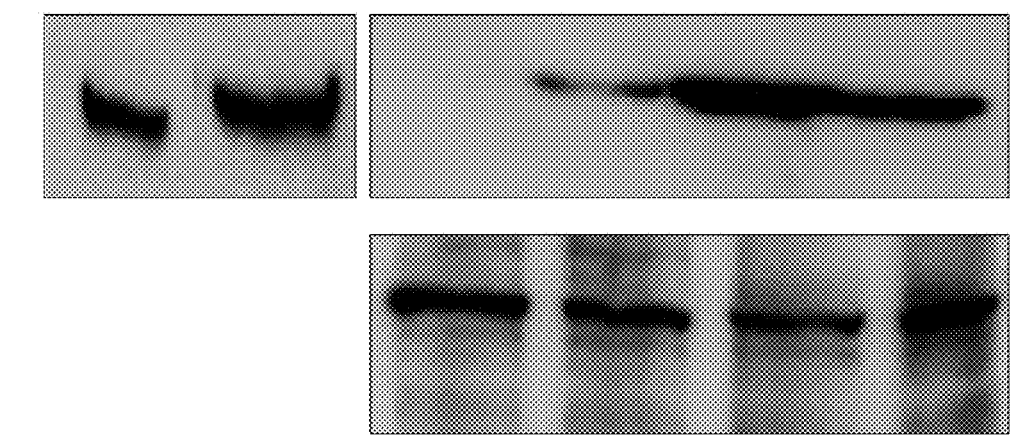

Three additional markers of hepatic epithelial cell differentiation were evaluated. These included the hepatocyte markers, H.4 antigen and α1-antitrypsin (AAT), and the bile duct marker cytokeratin 7 (CK7; Table 3; Grisham and Thorgeirsson, 1987; Grompe and Feingold, 2001; Petersen et al., 1999). Examined conventional lines expressed H.4 and AAT but not CK7 (Table 3; FIG. 6). Xs-derived Lig-8 cells expressed all three markers, but only expression of H.4 (data not shown) and AAT (FIG. 6B) increased in Xs-free medium. Xs-derived Lig-13 cells showed very weak expression of the two hepatocyte markers that did not increase in Xs-free medium (Table 3; FIG. 6B). However, this line showed strong expression of CK7 that was modestly elevated in Xs-free medium (FIG. 6B).

Figure 7:
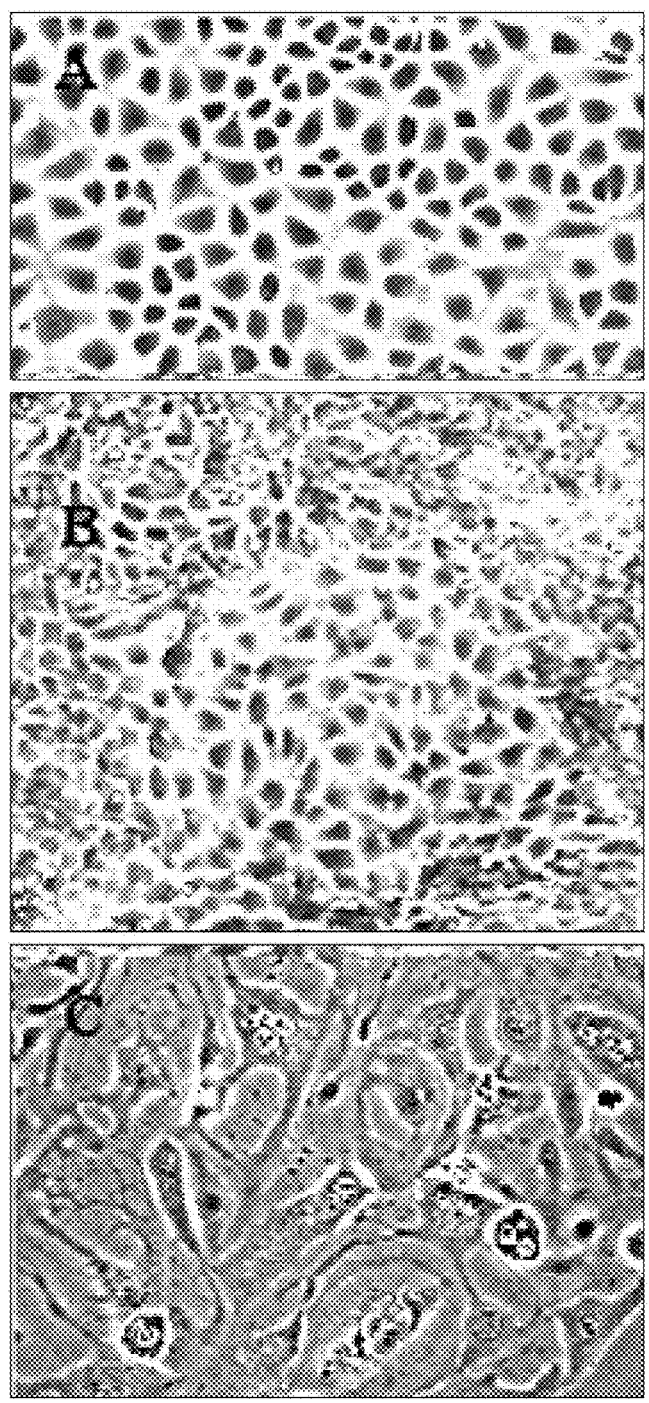
FIGS. 7A-7C are micrographs showing the production of binucleated cells by Lig-8 cells, a putative adult rat hepatocyte stem cell line. Shown are phase contrast micrographs of serum-reduced (1%) quiescent cultures of conventional Lig-1 (FIG. 7A) and SACK-derived Lig-8 (FIG. 7B) cells.

Evidence for Two Different Types of Hepatic Epithelial Stem Cell Lines Derived by SACK The analysis of lineage-specific marker proteins suggested that Xs-derived Lig-8 cells and Lig-13 cells might produce progeny cells with respective hepatocyte and cholangiocyte properties. Subsequent analyses supported this conclusion. In general, Xs-derived lines were morphologically distinct from conventional lines. Conventional cells maintained a homogenous field of cells under conditions of active growth or quiescence (FIG. 7A). In contrast, Xs-derived cells showed a heterogeneous field of cells that became contoured after 2 weeks of quiescence (FIG. 7B). Interestingly, although quiescent Lig-8 cells appear highly compact and small, these cell layers produce a unique type of large cells found in suspension. The large cells were adherent on collagen coated dishes and had a distinct morphology from cells in the monolayer from which they arose. Most were binucleated (FIG. 7C), a feature of mature hepatocytes (Sigler, 1995).

When conventional Lig-1 and Lig-3 cells were compared to Xs-derived Lig-8 and Lig-13 cells for formation of spheroid aggregates, only Lig-8 and Lig-13 formed spheroids of significant size, with Lig-8 being superior (data not shown). Spheroid formation is property of mature hepatocytes in culture (Mitaka et al., 1999; Powers et al., 1997). As an indicator hepatocyte enzymatic activity, we evaluated cytochrome p450 1A1 activity in Lig-8 cells using the ethoxyresorufin oxidation assay (Coumoul et al., 2001). In Xs-free medium, Lig-8 cells had a mean ethoxyresorufin-o-deethylase (EROD) activity of 180 nanomoles converted/cell/hour. This activity level compared favorably to that of freshly isolated rat hepatocytes which was 7.4-fold greater.

In the course of evaluating the hepatic cell lines for in vitro cell transformation properties, a unique property of Lig-13 cells was observed. In soft agar culture, Lig-1, Lig-2 and Lig-8 cells showed no growth. In contrast, Lig-13 cells produced tubular structures that appeared to have lumens in phase micrographs (FIG. 8). The growth of such structures is indicative of bile duct epithelium cell differentiation (Joplin, 1994). These structures are distinct from the spherical colonies formed in soft agar by neoplastic cells.

EXAMPLE 2

As described herein, Lig-8 is a stable adult stem cell line that was derived from the nonparenchymal cell fraction of collagenase-perfused adult rat liver. Lig-8 cells can be stably propagated in culture for periods exceeding 50 culture passages without evidence of neoplastic cell transformation as determined by soft agar colony formation studies in tumor formation studies in SCID mice.

Serum Requirements

Lig-8 cells were initially clonally derived in medium supplemented with 10% dialyzed fetal bovine serum and 400 μM xanthosine. They are routinely maintained in the same medium. The cells will also continue to proliferate in culture medium supplemented with only 1% fetal bovine serum (FIG. 9), whereas conventionally-derived, non-SACK, clonal adult rat liver epithelial cell lines undergo growth arrest under these conditions. Lig-8 cells also arrest and die if no serum is provided at all.

Morphology

Under routine culture conditions, Lig-8 cells exhibit an epithelial morphology, forming epitheloid colonies and monolayers (FIG. 10A). The appearance of the cells is similar under conditions of 1% serum, but there are larger, more bi-nucleated cells observed (FIG. 10B). Although not a specific indicator of hepatocyte maturation, binucleation is a common feature of mature hepatocytes in vivo Hepatocytic Markers Expressed by Lig-8 Cells Under Routine Culture Conditions Hepatocytic proteins: Alpha-fetoprotein (AFP) and albumin are two major protein markers of cells in the hepatocytic lineage. During embryogenesis, the induction of albumin and AFP mRNA in the endodermal cells is the first evidence of hepatic differentiation. As the cell mature into hepatocytes, AFP production decreases, and the level of albumin expression increases. Therefore, the detection of both AFP and albumin proteins in Lig-8 cells is consistent with the hepatocytic lineage of this cell line. Lig-8 cells also express cytokeratin 8, a liver epithelial cell marker, and cytochrome p4501A1, an important detoxification enzyme expressed in mature hepatocytes (Table 4).

Hepatocyte transcription factors: The expression of three transcription factors, hepatocyte nuclear transcription factor (HNF)-3 and CAAT enhancer-binding proteins (CEBP)-alpha and -beta were analyzed in Lig-8 cells by immunoblotting. HNF3 proteins regulate a transcription factor network required for differentiation during mammalian liver and gut development (Kaestner, 2000). Immunoblotting for HNF3 protein revealed expression of this protein in Lig-8 cells. The CEBPs encompass a family of transcriptional factors that play an important role in regulating the expression of multiple hepatocyte-specific genes (Diehl, 1998). CEBP-alpha is the predominant CEBP isoform that is expressed by adult hepatocytes in healthy livers (Diehl, 1998). Constitutive expression of CEBP-beta is highest in the liver, intestine, lung and adipose tissue (Diehl, 1998). Lig-8 cells were shown to express both CEBP-alpha and CEBP-beta (Table 4).

Secretory proteins: Lig-8 cells also secrete AFP and albumin proteins, implying that cellular secretory pathways are active and functional in these cells. (Table 4 and FIG. 11).

Hepatocytic Markers Expressed by Lig-8 Cells Under Conditions of Induced Differentiation We examined growth-factor induced differentiation of Lig-8 cell cultures at both high and low cell densities in xanthosine-free medium. In previous studies with in vitro model cell lines, we showed that low cell density promotes asymmetric cell kinetics, which provide differentiating non-stem cell progeny cells while maintaining stem cell numbers (Rambhatla et al., 2001).

Differentiation Under Conditions of High Cell Density

For high cell density studies, Lig-8 cells were induced to differentiate by the addition of epidermal growth factor (EGF) and transforming growth factor-β (TGF-β) to cells at an initial density of 10,000 cells/cm². The cells were then cultured under the influence of the growth factors for 9 days, at which time morphological, cell kinetics, and molecular expression properties indicative of differentiation were evaluated.

Figures 12A, 12B, 12C:
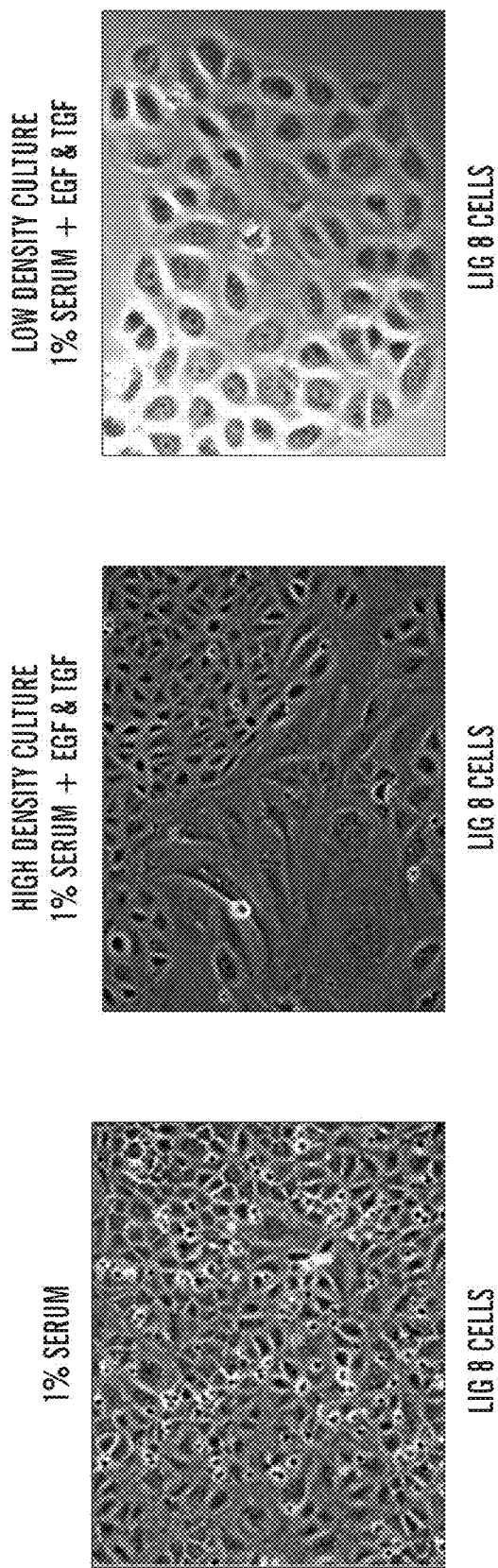
FIGS. 12A-C show the morphology of Lig-8 cells under high and low density differentiation.

Morphology: Lig-8 cells showed a heterogeneous response to the addition of the growth factors. Initially, all of the cells appeared unchanged, and therefore, resistant to effects of the growth factors. However, subsequently, some of the cells within the culture appeared to respond to EGF and TGF-β and displayed phenotypic features of cells undergoing differentiation, including enlargement of the cytoplasm and acquiring a bi-nucleated phenotype. At the same time, there were other cells in the culture that did not respond to the growth factors and retained their normal mononuclear, epitheloid morphology (FIG. 12). In contrast, conventionally derived, non-SACK adult rat liver epithelial cells lines showed uniform, complete, morphological differentiation.

Cell kinetics: The total number of cells present after 9 days of culture in the presence of EGF and TGF-β was used as a cell kinetics index (FIG. 13). Compared to conventional lines, Lig-8 cells showed only a modest (30%) reduction in overall cell growth rate. Expression of the proliferating cell nuclear antigen (PCNA), detected by immunoblotting (FIGS. 14A and 14B), was used as an additional indicator of the cell kinetics state of treated Lig-8 cells. The continued high level of expression of PCNA was indicative of a high fraction of cells in the cell cycle, despite treatment with EGF and TGF-β.

Figure 15A:
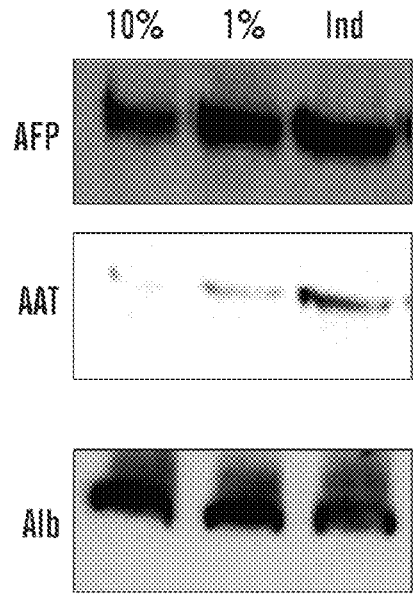
FIGS. 15A and 15B are immunoblots showing the expression of 3 hepatocytic proteins.
Figure 15B:
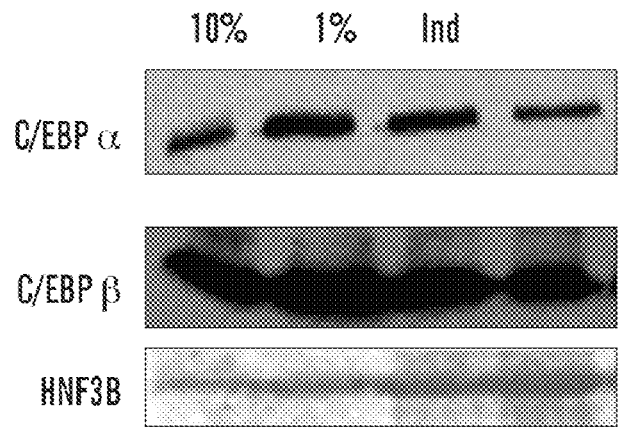

Hepatocytic markers: The expression of 3 hepatocytic proteins, AFP and albumin and alpha1-antitrypsin was analyzed in EGF and TGF-β-treated Lig-8 cells by immunoblotting. No significant changes were detected in the level of AFP or albumin under conditions of induced differentiation (FIG. 15). In contrast, alpha1-antitrypsin, which was almost undetectable in Lig-8 cells under routine culture conditions, was observed to be well expressed in response to growth factor treatment. The induction of alpha1-antitrypsin is indicative of increasingly mature hepatocytic differentiation by Lig-8 cells (FIG. 15; Table 5).

Transcription factors: The expression of three transcription factors, HNF3 and CEBP-alpha and -beta were analyzed by immunoblotting. No significant increase in HNF3 and CEBP-beta expression was observed. The expression of CEBP-alpha was modestly elevated by the reduction in serum concentration, whether or not the growth factors were added (FIG. 15; Table 5).

Differentiation Under Low Cell Density Conditions

The effect of EGF and TGF-β on Lig-8 cell differentiation was also evaluated at the lower cell density of 1000 cells/cm2. As in high cell density studies, the cells were cultured under the influence of the growth factors for 9 days before evaluation for indicators of differentiation. To date, only morphological and cell kinetics analyses have been performed.

Morphology: The majority of the cells in the growth factor-treated cultures were bi-nucleated (FIG. 12). Within the culture, there were a few epitheloid colonies still present.

Cell kinetics: Under conditions of low density, the Lig-8 cells showed a greater reduction (52%) in the overall cell growth rate, indicating a enhanced response to growth-arresting effects of EGF and TGF-β. This result is consistent with the expectation of increased asymmetric cell kinetics, producing growth factor-responsive differentiating progeny, at lower cell densities.

SUMMARY

Adult stem cells are defined by virtue of their functional properties. The most common attributes of adult stem cells include: (1) their lack of expression of mature differentiated markers; (2) their ability to produce differentiated progeny; (3) their ability to self-renew; and (4) their ability to expand their number conditionally.

The Lig-8 cell line meets all of these criteria. The SACK method exploits attribute #4 to expand adult rat hepatocytic stem cells in culture, while maintaining their ability to produce differentiating progeny. Lig-8 cells can be stably propagated in culture for periods exceeding 50 culture passages without evidence of neoplastic cell transformation as determined by soft agar colony formation studies and tumor formation studies in SCID mice. We interpret the morphologically heterogeneous cultures observed in Lig-8 cell cultures after the addition of EGF and TGF-β to manifest a mixture of cycling stem cells (undifferentiated cells; unresponsive to growth factors) and the differentiating progeny cells that they produce by asymmetric division (differentiated cells; responsive to the growth factors).

REFERENCES

Alpini G, Phillips J O, Vroman B, LaRusso, N F. 1994. Recent advances in the isolation of liver cells. Hepatology 20:494-514.

Clarke J, Porter A J, Thorpe R, Davis J M. 2002. Cloning. In: Davis J M, editor. Basic Cell Culture. Oxford: Oxford University Press. p 290-291.

Coumoul X, Diry M, Robillot C, Barouki R. 2001. Differential regulation of cytochrome P450 1A1 and 1B1 by a combination of dioxin and pesticides in the breast tumor cell line MCF-7. Cancer Res 61:3942-3948.

Diehl A M. Roles of CCAAT/enhancer-binding proteins in regulation of liver regenerative growth. *J Biol Chem.* 1998 Nov. 20; 273(47):30843-6.

Farber E. 1956. Similarities in the sequence of early histological changes induced in the liver of the rat by ethionine, 2-acetylaminofluorene, and 3'-methyl-4-dimethylaminoazobenzene. Cancer Res 16:142-155.

Fausto N, Lemire J M, Shiojiri N. 1993. Cell lineages in hepatic development and the identification of progenitor cells in normal and injured liver. Proc Soc Exp Biol Med 204:237-241.

Glimm H, Eaves C J. 1999. Direct evidence for multiple self-renewal divisions of human in vivo repopulating hematopoietic cells in short-term culture. Blood 94:2161-2168.

Grisham J W. 1995. Hepatic epithelial stem-like cells. Verh Dtsch Ges Pathol 79:47-54.

Grisham J W, Coleman W B, Smith G J. 1993. Isolation, culture, and transplantation of rat hepatocytic precursor (stem-like) cells. Proc Soc Exp Biol Med 204:270-279.

Grisham J W, Thorgeirsson S S. 1997. Liver stem cells. In: Potten C S, editor. Stem Cells. London: Academic Press. p 233-282.

Grompe M, Finegold M J. 2001. Liver stem cells. In: Marshak D R, Gardner R L, Gottlieb, D, editors. Stem cell biology. Cold Spring Harbor: Cold Spring Harbor Laboratory Press. p 455-497.

Haruna Y, Saito K, Spaulding S, Nalesnik M A, Gerber M A. 1996. Identification of bipotential progenitor cells in human liver development. Hepatology 23:476-481.

Hinds P W, Finlay C A, Frey A B, Levine A J. 1987. Immunological evidence for the association of p53 with a heat shock protein, hsc70, in p53-plus-ras-transformed cell lines. Mol Cellular Biol 7:2863-2869.

Jiang Y, Jahagirdar B N, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfaille C M. 2002. Pluripotency of mesenchymal stem cells derived from adult marrow. Nature 418: 41-49.

Joplin R. 1994. Isolation and culture of biliary epithelial cells. Gut 35:875-878.

Kaestner K H. The hepatocyte nuclear factor 3 (HNF3 or FOXA) family in metabolism. *Trends Endocrinol Metab.* 2000 September; 11(7):281-5.

Liu Y, Bohn S A, Sherley J L. 1998a. Inosine-5'-monophosphate dehydrogenase is a rate-determining factor for p53-dependent growth regulation. Mol Biol Cell 9:15-28.

Liu Y, Riley L B, Bohn S A, Boice J A, Stadler P B, Sherley J L. 1998b. Comparison of bax, waft, and IMP dehydrogenase regulation in response to wild-type p53 expression under normal growth conditions. J Cell Physiol 177:364-376.

Loeffler M, Potten C S. 1997. Stem cells and cellular pedigrees—a conceptual introduction. In: Potten C S, editor. Stem Cells. London: Academic Press. p 1-28.

McKay R. 2000. Stem cells—hype and hope. Nature 406: 361-364.

Merok J R, Sherley J L. 2001. Breaching the kinetic barrier to in vitro somatic stem cell propagation. J. Biomed Biotech 1:24-26.

Michalopoulos G K, Bowen W C, Zajac V F, Beer-Stolz D, Watkins S, Kostrubsky V, Strom S C. 1999. Morphogenetic events in mixed cultures of rat hepatocytes and nonparenchymal cells maintained in biological matrices in the presence of hepatocyte growth factor and epidermal growth factor. Hepatology 29:90-100.

Mitaka T, Sato F, Mizuguchi T, Yokono T, Mochizuki Y. 1999. Reconstruction of hepatic organoid by rat small hepatocytes and hepatic nonparenchymal cells. Hepatology 29:111-125.

Moore K A, Ema H, Lemischka I R. 1997. In vitro maintenance of highly purified, transplantable hematopoietic stem cells. Blood 89:4337-4347.

Petersen B E, Bowen W C, Patrene K D, Mars W M, Sullivan A K, Murase N, Boggs S S, Greenberger J S, Goff J P. 1999. Bone marrow as a potential source of hepatic oval cells. Science 284:1168-1170.

Plescia C, Rogler C, Rogler L. 2001. Genomic expression analysis implicates Wnt signaling pathway and extracellular matrix alterations in hepatic specification and differentiation of murine hepatic stem cells. Differentiation 68:254-269.

Potten C S, Morris R J. 1988. Epithelial stem cells in vivo. J. Cell Sci Suppl 10:45-62.

Powers M J, Rodriguez R E, Griffith L G. 1997. Cell-substratum adhesion strength as a determinant of hepatocyte aggregate morphology. Biotechnol Bioeng 53:415-426.

Rambhatla L, Bohn S A, Stadler P B, Boyd J T, Coss R A, Sherley J L. 2001. Cellular senescence: ex vivo p53-dependent asymmetric cell kinetics. J. Biomed Biotech 1:27-36.

Sell S. 2001. Heterogeneity and plasticity of hepatocyte lineage cells. Hepatology 33:738-750.

Sherley J L. 1991. Guanine nucleotide biosynthesis is regulated by the cellular p53 concentration. Biol Chem 266: 24815-24828.

Sherley J L, Stadler P B, Johnson D R. 1995a. Expression of the wild-type p53 antioncogene induces guanine nucleotide-dependent stem cell division kinetics. Proc Natl Acad Sci USA 92:136-140.

Sherley J L, Stadler P B, Stadler J S. 1995b. A quantitative method for the analysis of mammalian cell proliferation in culture in terms of dividing and non-dividing cells. Cell Prolif 28:137-144.

Sigal S H, Brill S, Fiorino A S, Reid L M. 1992. The liver as a stem cell and lineage system. Am J Physiol 263:G139-G148.

Sigler S H. 1995. Evidence for a terminal differentiation process in the rat liver. Differentiation 59:35-42.

Spradling A, Drummond-Barbosa D, Kai T. 2001. Stem cells find their niche. Nature 414:98-104.

Thomson J A, Itskovitz-Eldor J, Shapiro S S, Waknitz M A, Swiergiel J J, Marshall V S, Jones J M. 1998. Embryonic stem cell lines derived from human blastocysts. Science 282:1145-1147.

Toma J G, Akhavan M, Fernandes K J, Barnabe-Heider F, Sadikot A, Kaplan D R, Miller F D. 2001. Isolation of multipotent adult stem cells from the dermis of mammalian skin. Nat Cell Biol 3:778-784.

Vogel G V. 2001. Can adult stem cells suffice? Science 292: 1820-1822.

Young P R, Tilghman, S M. 1986. The evolution of the AFP and albumin genes. In Hardie D G, Coggins J R, editors. Multidomain proteins—structure and evolution. Amsterdam: Elsevier Science. p 55-83.

Zaret K S. 1996. Molecular genetics of early liver development. Annu Rev Physiol 58:231-251.

All references described herein are incorporated herein by reference.

TABLE 1

Colony formation efficiency of adult rat liver epithelial cell lines[1]

| CELL STRAIN | CULTURE CONDITION | | |
|---|---|---|---|
| | Xs−<br>(Mean % ± SD; n = 6) | Xs+ | Xs+/Xs−<br>Ratio |
| Conventional Lines | | | |
| Lig-1 | 11 ± 3.4 | 9.8 ± 2.2 | 0.9 |
| Lig-2 | 28 ± 2.6 | 29 ± 3.7 | 1.0 |
| Lig-3 | 18 ± 2.8 | 18 ± 3.7 | 1.0 |
| Xs-derived cell lines ([Xs]) | | | |
| Lig-4 (400 μM) | 5.2 ± 2.4 | 8.0 ± 1.1 | 1.5 |
| Lig-6 (400 μM) | 3.9 ± 1.6 | 5.3 ± 1.8 | 1.4 |
| Lig-7 (400 μM) | 0.0 ± 0.0 | 6.7 ± 2.2 | ≧22 |
| Lig-8 (400 μM) | 1.3 ± 0.53 | 22 ± 3.6 | 17 |
| Lig-9 (400 μM) | 9.7 ± 3.4 | 11 ± 2.6 | 1.1 |
| Lig-13 (200 μM) | 0.3 ± 0.26 | 12 ± 2.7 | 40 |
| Lig-14 (200 μM) | 0.3 ± 0.42 | 0.4 ± 0.67 | 1.3 |
| Lig-15 (200 μM) | 1.9 ± 1.4 | 10 ± 1.6 | 5.3 |

Table 1 Legend

[1]Each cell strain was plated at 200 cells per each well of two 6-well plates in their respective culture medium used for propagation. Xs concentrations for Xs-derived lines are given in parentheses after cell line name. After 16 hours, one plate was replaced with X-free medium (Xs−) and the other plate was replaced with medium containing 50 μM xanthosine (Xs+). Plates were incubated for 14 days and then fixed and stained with crystal violet. Colonies detected by visual inspection were counted to determine the colony formation efficiency ([colony number/200] × 100%). Data are presented as the mean % ± standard deviation of 6 replicate wells.

TABLE 2

Fc(t) assay for detection of asymmetric cell kinetics by rat liver epithelial cell lines[1]

A. In Xs-free medium

| Cell Line | Fc(t)<br>(Mean ± S.E. [N]) | Terminal Division Fraction[2]<br>(Mean ± S.E. [N]) |
|---|---|---|
| Conventional<br>(Lig-1, 2, 3)[3] | 0.73 ± 0.06 (3)<br>p = 0.134 | 0.26 ± 0.08 (3)<br>p = 0.014 |
| Xs-derived<br>(Lig-8, 9, 13, 15)[4] | 0.51 ± 0.10 (3) | 0.69 ± 0.08 (4) |

B. Line Lig-9 Xs-dependence[5]

| Condition | Fc(t) | Terminal Division Fraction[2]<br>(Mean ± S.E. [n]) |
|---|---|---|
| Xs− | 0.45 ± 0.32 (14)<br>p = 0.006 | 0.58 |
| Xs+ | 1.1 ± 0.77 (29) | 0.47 |

Table 2 Legend

[1]Fc(t) values were determined for 2 GT periods as described (Sherley et al., 1995a). The expected value for symmetric kinetics is 1.0; the expected value for asymmetric cell kinetics is 0.42.
[2]Fraction of marked 2-cell microcolonies that show no division during the exam period of 5 days.
[3]The mean Fc(t) values determined in independent analyses of the indicated conventional cell lines were averaged. Data are presented as the mean ± standard error of N averaged analyses. The total numbers of microcolonies evaluated were 36, 26, and 28, respectively. Fc(t) determinations were based on 26, 23, and 17 dividing microcolonies, respectively.
[4]The mean Fc(t) values determined in independent analyses of the indicated Xs-derived cell lines were averaged. The total numbers of microcolonies evaluated were 11, 32, 10, and 12 respectively. Since Lig-15 exhibited only one dividing colony, it was not included in the Fc(t) analysis. The other Fc(t) analyses were based on 4, 14, and 4 dividing microcolonies, respectively.
[5]Xs-derived Lig-9 cells were evaluated in the presence (+) and absence (−) of Xs. The Xs− data are also included in the averaged analyses in A ("Xs-derived"). Fc(t) data are presented as the mean value ± standard deviation of n number of dividing microcolony analyses.
p = statistical significance level for observed differences between vertically compared groups.

TABLE 3

Expression of differentiation markers by adult rat hepatic epithelial cell lines

| | Conventional | | | Xs-derived | | | | | |
|---|---|---|---|---|---|---|---|---|---|
| | 1 | 2 | 3 | 5 | 7 | 8 | 9 | 13 | 15 |
| Non-epithelial | | | | | | | | | |
| ED-1[1] (Kupffer cells) | − | nd | nd | nd | nd | − | − | nd | nd |
| GFAP[1] (stellate cells) | − | nd | nd | nd | nd | − | − | nd | nd |
| Hepatocyte | | | | | | | | | |
| α-Fetoprotein (AFP)[2] | + | + | + | + | + | +! | nd | +* | + |
| AFP secretion[2] | + | + | nd | nd | nd | + | nd | + | nd |
| Albumin (ALB)[2] | + | + | nd | nd | nd | +! | nd | +* | nd |
| ALB secretion[2] | + | + | nd | nd | nd | + | nd | − | nd |
| α1-Antitrypsin (AAT)[2] | + | + | nd | nd | nd | +! | nd | +/−* | nd |
| H.4[3,4] | +* | nd | +/−* | nd | nd | +! | nd | +/−* | nd |
| CYP1A1 | nd | nd | nd | nd | nd | + | nd | nd | nd |
| Spheroid formation | − | nd | − | nd | nd | + | nd | +/− | nd |
| Binucleated cells[4] | − | − | nd | nd | nd | + | − | − | nd |
| Cholangiocyte | | | | | | | | | |
| Cytokeratin 7 (CK7)[2] | − | − | nd | nd | nd | +* | nd | +! | nd |
| Tubular structures | − | nd | nd | nd | nd | − | − | + | nd |

Table 3 Legend nd = not done;
− = no expression detected;
+/− = weak expression;
+ = expression detected;
! = increased expression in Xs-free conditions;
* = no increased expression in Xs-free conditions.
[1]Detected by immunohistochemistry.
[2]Detected by immunoblot analysis.
[3]Detected by in situ immunofluorescence analysis.
[4]Analyzed after confluent growth arrest in reduced serum (1%) for 1-2 weeks.

TABLE 4

Hepatocytic markers exhibited by Lig-8
cells under routine culture conditions

| Markers |
| --- |
| AFP |
| Albumin |
| C/EBP a |
| C/EBP b |
| HNF3 |
| CK8 |
| Cytochrome p450 1A1 |
| Albumin secretion |
| AFP secretion |

TABLE 5

Changes in hepatocytic markers in Lig
8-cells during induced differentiation

| Markers | Expression Result |
| --- | --- |
| AFP | No change |
| Albumin | No change |
| alpha-1 anti-trypsin | Marked increase |
| C/EBP alpha | Slight increase (serum only) |
| C/EBP beta | No change |
| HNF3 | No change |

What is claimed is:

1. A method of preparing hepatic cells that express mature hepatic cell markers comprising:
  a) culturing a population of cells from liver tissue obtained from a mammal, wherein the population of cells comprises stellate cells, hepatocytes, cholangiocytes, oval cells, Kupffer cells, sinusoidal endothelial cells and hepatic precursor cells,
  b) enriching the population of cells for hepatic precursor cells,
  c) culturing the enriched population of cells in a first culture medium comprising a guanine nucleotide precursor of at least 50 µM, or an analogue or derivative thereof, wherein said guanine nucleotide precursor suppresses asymmetric cell kinetics thereby allowing exponential growth of said hepatic precursor cells;
  d) passaging said cultured hepatic precursors in the culture medium of step (c) to allow expansion of said hepatic precursor cells; and
  e) contacting the expanded hepatic precursors of step (c) with a second culture medium that is free from the guanine nucleotide precursor of the first medium, and selecting cells with expression of a mature hepatic cell marker, wherein the hepatic cell marker is selected from the group consisting of: H4 antigen, α1-antitrypsin (AAT), cytokeratin 7 (CK7), cytokeratin 8 (CK8), albumin cytochrome p450 1A1, hepatocyte nuclear transcription factor (HNF-3), CAAT enhancer-binding protein (CEBP)-alpha and CAAT enhancer-binding protein (CEBP)-beta.

2. The method of claim 1, wherein the second culture medium comprises growth factors.

3. The method of claim 1, wherein said guanine nucleotide precursor is present in an amount of 50-400 µM.

4. The method of claim 1, wherein the cells of step c) are cultured for a period of time exceeding 50 culture passages under conditions where the hepatic precursors cells show no evidence of neo-plastic transformation.

5. The method of claim 1, wherein the cells of step c) a cultured for at least 80 cell doublings.

6. The method of claim 1, wherein cells of step c) are cultured at a cell density of at least 1000 cells per square centimeter.

* * * * *